US010907216B2

(12) United States Patent
Tanaka et al.

(10) Patent No.: US 10,907,216 B2
(45) Date of Patent: Feb. 2, 2021

(54) PREDICTION OF HEPATOCELLULAR CARCINOMA ONSET AFTER CLEARANCE OF HEPATITIS C VIRUS

(71) Applicant: PUBLIC UNIVERSITY CORPORATION NAGOYA CITY UNIVERSITY, Nagoya (JP)

(72) Inventors: Yasuhito Tanaka, Nagoya (JP); Kentaro Matsuura, Nagoya (JP)

(73) Assignee: PUBLIC UNIVERSITY CORPORATION NAGOYA CITY UNIVERSITY, Nagoya (JP)

( * ) Notice: Subject to any disclaimer, the term of this patent is extended or adjusted under 35 U.S.C. 154(b) by 0 days.

(21) Appl. No.: 16/097,954

(22) PCT Filed: Mar. 31, 2017

(86) PCT No.: PCT/JP2017/013525
§ 371 (c)(1),
(2) Date: Oct. 31, 2018

(87) PCT Pub. No.: WO2017/191720
PCT Pub. Date: Nov. 9, 2017

(65) Prior Publication Data
US 2019/0093173 A1 Mar. 28, 2019

(30) Foreign Application Priority Data
May 6, 2016 (JP) ................. 2016-093483

(51) Int. Cl.
C12Q 1/6886 (2018.01)
G01N 33/50 (2006.01)
C12N 15/09 (2006.01)
G01N 33/53 (2006.01)
G01N 33/68 (2006.01)
C12Q 1/68 (2018.01)

(52) U.S. Cl.
CPC ........... *C12Q 1/6886* (2013.01); *C12N 15/09* (2013.01); *C12Q 1/68* (2013.01); *G01N 33/50* (2013.01); *G01N 33/53* (2013.01); *G01N 33/68* (2013.01); *C12Q 2600/118* (2013.01); *C12Q 2600/156* (2013.01)

(58) Field of Classification Search
None
See application file for complete search history.

(56) References Cited

U.S. PATENT DOCUMENTS

2005/0255485 A1* 11/2005 Livak .................. C12Q 1/6827
435/6.17
2007/0048756 A1* 3/2007 Mei ..................... C12Q 1/6883
435/6.11

FOREIGN PATENT DOCUMENTS

WO 2012/108527 A1 8/2012
WO 2013/030786 A1 3/2013

OTHER PUBLICATIONS

Tanaka (Nature Genetics vol. 41 No. 10 Oct. 2009 pp. 1105-1111).*
Lucentini (The Scientist 2004 vol. 18 pp. 1-3).*
Wacholder et al (J. Natl. Cancer Institute 2004vol. 96 pp. 434-442).*
Degasperi (J Viral Hepat Jun. 8, 2019 pp. 1-4).*
GenBank (db SNP entry rs17047200 added with build 123 on Oct. 28, 2004).*
Matsuura (Gastroenterology 2017 vol. 152 pp. 1383-1394 and published online Feb. 3, 2017).*
Syvanen (Nature Reviews Genetics Dec. 2001 vol. 2 pp. 930-942).*
Kato (Hepatology vol. 42 No. 4 2005).*
R. Lozano et al., "Global and regional mortality from 235 causes of death for 20 age groups in 1990 and 2010: a systematic analysis for the Global Burden of Disease Study 2010," Lancet 2012, vol. 380, pp. 2095-2128.
G. L. Davis et al., "Aging of hepatitis C virus (HCV)-infected persons in the United States: a multiple cohort model HCV prevalence and disease progression," Gastroenterology 2010, vol. 138, 513-521, 521 e1-e6.
K. R. Reddy et al., "Ledipasvir and sofosbuvir in patients with genotype 1 hepatitis C virus infection and compensated cirrhosis: An integrated safety and efficacy analysis," Hepatology 2015, vol. 62, pp. 79-86.
N. Hiramatsu et al., "Suppression of hepatocellular carcinoma development in hepatitis C patients given interferon-based antiviral therapy," Hepatology Research 2015, 45, pp. 152-161.
A. Makiyama et al., "Characteristics of Patients with Chronic Hepatitis C who Develop Hepatocellular Carcinoma after a Sustained Response to Interferon Therapy," Cancer, Oct. 1, 2004, vol. 101, No. 7, pp. 1616-1622.
K-C Chang et al., "A novel predictive score for hepatocellular carcinoma development in patients with chronic hepatitis C after sustained response to pegylated interferon and ribavirin combination therapy," J Antimicrob Chemother, 2012, 67, pp. 2766-2772.
A. Sato et al., "Clinical Characteristics of Patients who Developed Hepatocellular Carcinoma after Hepatitis C Virus Eradication with Interferon Therapy: Current Status in Japan," Internal Medicine, 2013, 52, pp. 2701-2706.
Y. Arase et al., "Effect of Type 2 Diabetes on Risk for Malignancies Includes Hepatocellular Carcinoma in Chronic Hepatitis C," Hepatology 2013, vol. 57, No. 3, pp. 964-973.
K. Matsuura et al., "Role of IL28B for chronic hepatitis C treatment toward personalized medicine," Journal of Gastroenterology and Hepatology, 2014, 29, pp. 241-249.

(Continued)

*Primary Examiner* — Amanda Haney
(74) *Attorney, Agent, or Firm* — Locke Lord LLP

(57) ABSTRACT

The present invention addresses the problem of how to provide a predictive marker useful for carcinogenesis surveillance after hepatitis C virus eradication. Provided is a predictive marker composed of a single nucleotide polymorphism specified by rs17047200. In the present invention, the single nucleotide polymorphism is detected in nucleic acid samples collected from subjects, thereby to examine the risk of developing hepatocellular carcinoma after of hepatitis C virus eradication.

4 Claims, 19 Drawing Sheets

Specification includes a Sequence Listing.

(56) References Cited

OTHER PUBLICATIONS

K. Matsuura et al., "Host Genetic Variants Influencing the Clinical Course of Hepatitis C Virus Infection," Journal of Medical Virology, 2016, 88, pp. 185-195.
L. Prokunina-Olsson et al., "A variant upstream of IFNL3 (IL28B) creating a new interferon gene IFNL4 is associated with impaired clearance of hepatitis C virus," Nature Genetics, Feb. 2013, vol. 45, No. 2, pp. 164-171, doi:10.1038/ng.2521 (2 pages).
A. Rauch et al., "Genetic Variation in IL28B Is Associated With Chronic Hepatitis C and Treatment Failure: A Genome-Nide Association Study," Gastroenterology 2010,138, pp. 1338-1345, 1345 e1-e7.
D. L. Thomas et al., "Genetic variation in IL28B and spontaneous clearance of hepatitis C virus," Nature, Oct. 8, 2009, vol. 461, pp. 798-801, doi:10.1038.
J. Fellay et al., "ITPA gene variants protect against anaemia in patients treated for chronic hepatitis C," Nature, Mar. 18, 2010, vol. 464, pp. 405-408.
Y. Tanaka et al., "Genome-wide association study identified ITPA/DDRGK1 variants reflecting thrombocytopenia in pegylated interferon and ribavirin therapy for chronic hepatitis C," Human Molecular Genetics, 2011, vol. 20, No. 17, pp. 3507-3516.
E. Iio et al., "Genome-wide association study identifies a PSMD3 variant associated with neutropenia in interferon-based therapy for chronic hepatitis C," Human Genetics, 2015, 134, pp. 279-289 (20 pages in total).
E. Patin et al., "Genome-Wide Association Study Identies Variants Associated With Progression of Liver Fibrosis From HCV Infection," Gastroenterology, 2012, 143, pp. 1244-1252 e1-e12.
Y. Urabe et al., "A genome-wide association study of HCV-induced liver cirrhosis in the Japanese population identifies novel susceptibility loci at the MHC region," Journal of Hepatology, 2013, vol. 58, pp. 875-882.
V. Kumar et al., "Genome-wide association study identifies a susceptibility locus for HCV-induced hepatocellular caranoma," Nature Genetics, May 2011, vol. 43, No. 5, pp. 455-458, doi:10.1038/ng809.
D. Miki et al., "Variation in the DEPDC5 locus is associated with progression to hepatocellular carcinoma in chronic hepatitis C virus carriers," Nature Genetics, Aug. 2011, vol. 43, No. 8, pp. 797-800, doi:10.1038/ng876.
N. Nishida et al., "Further development of multiplex single nucleotide polymorphism typing method, the DigiTag2 assay," Analytical Biochemistry, 2007, 364, pp. 78-85.
R. Berry et al., "Structural and functional evidence for a substrate exclusion mechanism in mammalian tolloid like-1 (TLL-1) proteinase," FEBS Letters, 2010, 584, pp. 657-661.
NCBI, "sbSNP Short Genetic Variations," ss 276972898 (2 pages).
K. Matsuura et al., "Genome-Wide Association Study Identifies TLL1 Variant Associated With Development of Hepatocellular Carcinoma After Eradication of Hepatitis C Virus Infection," Gastroenterology, May 2017, vol. 152, No. 6, pp. 1383-1394.
International Search Report dated Jun. 27, 2017, issued for PCT/JP2017/013525.
Supplementary European Search Report dated Oct. 28, 2019, issued for the European patent application No. 17792653.2.

* cited by examiner

|  | GWAS | | Replication cohort | | |
| --- | --- | --- | --- | --- | --- |
|  | G-Case (n = 123) | G-CTRL (≥5y) (n = 333) | R-Case (n = 130) | R-CTRL (≥5y) (n = 210) | R-CTRL (≥3y) (n = 356) |
| Pretreatment | | | | | |
| Gender, male / female | 93 / 30 | 176 / 157 | 100 / 30 | 106 / 104 | 175 / 181 |
| Age, years | 60 (57 – 66) | 58 (51 – 64) | 61 (56 – 66) | 58 (50 – 65) | 59 (50 – 65) |
| Hemoglobin, g/dL | 13.8 (12.9 – 14.7) | 14.1 (13.3 – 15.0) | 13.9 (13.1 – 14.8) | 13.8 (12.8 – 15.0) | 13.8 (12.8 – 14.8) |
| Platelet count, ×$10^9$/L | 127 (104 – 155) | 165 (132 – 198) | 125 (106 – 145) | 170 (131 – 204) | 170 (134 – 208) |
| ALT, IU/L | 76 (49 – 113) | 58 (35 – 100) | 73 (48 – 124) | 56 (34 – 103) | 47 (31 – 92) |
| γ-GTP, IU/L | 41 (31 – 91) | 31 (19 – 55) | 51 (29 – 89) | 38 (23 – 58) | 33 (19 – 55) |
| Albumin, g/dl | 3.9 (3.7 – 4.1) | 4.2 (3.9 – 4.4) | 4.0 (3.8 – 4.2) | 4.1 (3.9 – 4.4) | 4.1 (3.9 – 4.4) |
| AFP, ng/mL | 7.7 (4.5 – 18.0) | 4.8 (3.1 – 7.4) | 10.3 (6.0 – 19.0) | 4.1 (2.3 – 7.2) | 4.1 (2.7 – 7.4) |
| APRI | 1.65 (0.91 – 2.49) | 0.90 (0.52 – 1.44) | 1.35 (0.98 – 2.26) | 0.81 (0.50 – 1.43) | 0.72 (0.43 – 1.41) |
| FIB-4 | 3.73 (2.59 – 4.92) | 2.30 (1.48 – 3.27) | 3.87 (2.51 – 5.00) | 2.16 (1.49 – 3.23) | 2.15 (1.31 – 3.27) |
| HCV RNA, log IU/mL | 5.4 (4.7 – 6.3) | 6.2 (5.7 – 6.6) | 5.5 (4.6 – 6.3) | 6.1 (5.3 – 6.7) | 6.1 (5.3 – 6.8) |
| HCV genotype, 1 / 2 / 3 / N.A. | 64 / 37 / 0 / 22 | 246 / 86 / 0 / 1 | 68 / 45 / 0 / 17 | 116 / 88 / 1 / 5 | 205 / 143 / 1 / 7 |
| Liver fibrosis, F0-2 / F3-4 / N.A. | 39 / 48 / 36 | 239 / 64 / 30 | 40 / 52 / 38 | 137 / 39 / 34 | 214 / 62 / 80 |
| Body mass index | 22.7 (21.1 – 24.6) | 23.2 (21.5 – 25.3) | 23.5 (21.1 – 25.6) | 23.0 (20.9 – 25.2) | 22.8 (20.7 – 24.9) |
| Diabetes, + / – / N.A. | 25 / 65 / 33 | 30 / 242 / 61 | 24 / 81 / 25 | 19 / 184 / 7 | 29 / 305 / 22 |
| Anti-HBc, + / – / N.A. | 49 / 47 / 27 | 75 / 157 / 101 | 51 / 55 / 24 | 53 / 123 / 34 | 96 / 213 / 47 |
| 6 months after the end of treatment | | | | | |
| ALT, IU/L | 21 (15 – 28) | 16 (13 – 20) | 23 (15 – 36) | 18 (14 – 26) | 17 (12 – 24) |
| AFP, ng/mL | 4.4 (2.8 – 6.5) | 3.1 (2.1 – 4.4) | 4.2 (3.0 – 6.6) | 3.0 (2.0 – 4.0) | 3.0 (2.1 – 4.2) |
| APRI | 0.57 (0.38 – 0.90) | 0.37 (0.28 – 0.52) | 0.60 (0.44 – 0.85) | 0.38 (0.27 – 0.54) | 0.34 (0.26 – 0.51) |
| FIB-4 | 2.76 (2.00 – 3.83) | 1.87 (1.32 – 2.44) | 2.68 (1.98 – 3.81) | 1.79 (1.22 – 2.54) | 1.79 (1.21 – 2.47) |
| Regimen | | | | | |
| PEG-IFN+RBV / IFN+RBV / IFN mono / PI+PEG-IFN+RBV / N.A. | 52 / 13 / 54 / 4 / 0 | 298 / 17 / 18 / 0 / 0 | 53 / 6 / 64 / 4 / 3 | 167 / 5 / 37 / 1 / 0 | 298 / 5 / 42 / 11 / 0 |
| Period of observation | | | | | |
| Period from end of treatment to diagnosis of HCC, months | 61 (31 – 96) | -- | 62 (38 – 116) | -- | -- |
| Period from end of treatment to last follow-up, months | -- | 89 (78 – 119) | -- | 71 (64 – 119) | 61 (42 – 89) |

*Fig. 2*

| Primer / Probe | Sequence |
| --- | --- |
| Forward primer | 5'-AACTCCATTCCAAGCATTTACCAGAAAATAAAATTCTGTA-3' (SEQ ID NO: 2) |
| Reverse primer | 5'-ACCTCATATAATTTAGAATTATAGTTCATCACTCATTAACCCTA-3' (SEQ ID NO: 3) |
| Query probe for major allele (A) | 5'-ACCACCGCTTGAATACAAAACATCTTCAGAAATAGATGTCAATGtACA-3' (SEQ ID NO: 4) |
| Query probe for minor allele (T) | 5'- CCGTGTCCACTCTAGAAAAACCTTCAGAAATAGATGTCAATGtACT-3' (SEQ ID NO: 5) |
| Common probe | 5'-GTGAAATGGACATAAGTGGGCAAAAAAAAAAAAGAGTTCATGGACGTAATGTAAGTGAGCA-3' (SEQ ID NO: 6) |

*Fig. 3*

| Primer / Probe | Sequence |
|---|---|
| Forward primer | 5'-GCTCGTATGTCATTTCAACTCTTTTT-3' (SEQ ID NO: 7) |
| Reverse primer | 5'-CCTGACCTTGCCTTCAGAAATAG-3' (SEQ ID NO: 8) |
| Probe for major allele (A): VIC | 5'-CCATTTCACAGTTCATT-3' (SEQ ID NO: 9) |
| Probe for minor allele (T): FAM | 5'-TCCATTTCACTGTTCAT-3' (SEQ ID NO: 10) |

*Fig. 4*

| dbSNP rsID | Chr | Nearest gene | Risk allele | Allele (1/2) | Stage | Case (n = 253) | | | CTRL (≥5y) (n = 543) | | | OR (95% CI) | P-value |
|---|---|---|---|---|---|---|---|---|---|---|---|---|---|
| | | | | | | 11 | 12 | 22 | 11 | 12 | 22 | | |
| rs17047200 | 4 | TLL1 | T | T/A | GWAS | 7 | 31 | 85 | 0 | 57 | 275 | 2.38 (1.56-3.64) | $3.74 \times 10^{-5}$ |
| | | | | | Replication [a] | 5 | 37 | 88 | 1 | 34 | 175 | 2.35 (1.48-3.75) | $2.33 \times 10^{-4}$ |
| | | | | | Combined [b] | 12 | 68 | 173 | 1 | 91 | 450 | 2.37 (1.74-3.23) | $2.66 \times 10^{-8}$ |

*Fig. 7*

| Risk factor | HR (95% CI) | P-value |
| --- | --- | --- |
| Univariate Analysis | | |
| Gender, male / female | 1.99 (1.49-2.67) | <0.001 |
| Age (by every 10 years) | 1.65 (1.42-1.93) | <0.001 |
| Platelet count (by every $10^{10}$/L) | 0.85 (0.83-0.88) | <0.001 |
| γ-GTP (by every 40 IU/L) | 1.12 (1.06-1.19) | <0.001 |
| Albumin (by every 1 g/dL) | 0.25 (0.17-0.37) | <0.001 |
| Pre-ALT (by every 40 IU/L) | 1.02 (0.95-1.09) | 0.643 |
| Pre-AFP (by every 10 ng/mL) | 1.02 (1.00-1.03) | 0.020 |
| Pre-APRI (by every 1 unit) | 1.29 (1.19-1.41) | <0.001 |
| Pre-FIB-4 (by every 1 unit) | 1.33 (1.27-1.40) | <0.001 |
| Fibrosis, F3-4 / F0-2 | 3.23 (2.39-4.32) | <0.001 |
| HCV genotype, 1 / 2 | 0.85 (0.64-1.12) | 0.234 |
| rs17047200, AT+TT / AA | 1.81 (1.39-2.37) | <0.001 |
| Body mass index, (by every 1 unit) | 0.99 (0.95-1.04) | 0.828 |
| Diabetes, + / − | 2.62 (1.89-3.62) | <0.001 |
| Anti-HBc, + / − | 1.57 (1.19-2.08) | 0.001 |
| Post-ALT (by every 40 IU/L) | 1.39 (1.11-1.74) | 0.004 |
| Post-AFP (by every 10 ng/mL) | 2.52 (2.02-3.13) | <0.001 |
| Post-APRI (by every 1 unit) | 1.88 (1.59-2.23) | <0.001 |
| Post-FIB-4 (by every 1 unit) | 1.18 (1.13-1.22) | <0.001 |
| Multivariate Analysis | | |
| Gender, male / female | 2.19 (1.39-3.44) | <0.001 |
| Age (by every 10 years) | 1.44 (1.13-1.83) | 0.003 |
| Albumin (by every 1 g/dL) | 0.31 (0.19-0.53) | <0.001 |
| Fibrosis, F3-4 / F0-2 | 1.63 (1.07-2.48) | 0.024 |
| rs17047200, AT+TT / AA | 1.78 (1.17-2.70) | 0.008 |
| Diabetes, + / − | 1.91 (1.21-3.03) | 0.006 |
| Post-AFP (by every 10 ng/mL) | 2.37 (1.71-3.30) | <0.001 |

*Fig. 9*

| Risk factor | HR (95% CI) | P-value |
|---|---|---|
| Univariate Analysis | | |
| Gender, male / female | 11.27 (1.51–83.94) | 0.018 |
| Age (by every 10 years) | 2.63 (1.53–4.51) | <0.001 |
| γ-GTP (by every 40 IU/L) | 1.21 (0.98–1.51) | 0.083 |
| Pre-ALT (by every 40 IU/L) | 1.09 (0.90–1.32) | 0.372 |
| Pre-AFP (by every 10 ng/mL) | 3.35 (1.50–7.45) | 0.003 |
| HCV genotype, 1 / 2 | 1.26 (0.51–3.12) | 0.619 |
| rs17047200, AT+TT / AA | 2.60 (1.10–6.16) | 0.030 |
| Body mass index, (by every 1 unit) | 0.89 (0.77–1.03) | 0.114 |
| Diabetes, + / − | 2.25 (0.75–6.77) | 0.147 |
| Anti-HBc, + / − | 3.22 (1.27–8.17) | 0.014 |
| Post-ALT (by every 40 IU/L) | 0.63 (0.15–2.69) | 0.531 |
| Post-AFP (by every 10 ng/mL) | 0.57 (0.04–8.35) | 0.678 |
| Multivariate Analysis | | |
| Age (by every 10 years) | 2.90 (1.52–5.54) | 0.001 |
| rs17047200, AT+TT / AA | 4.26 (1.56–11.70) | 0.005 |

*Fig. 10*

| Risk factor | HR (95% CI) | P-value |
| --- | --- | --- |
| Univariate Analysis | | |
| Gender, male / female | 1.09 (0.71–1.68) | 0.695 |
| Age (by every 10 years) | 1.34 (1.03–1.74) | 0.028 |
| Platelet count (by every $10^{10}$/L) | 0.93 (0.88–0.98) | 0.009 |
| γ-GTP (by every 40 IU/L) | 1.20 (1.05–1.37) | 0.009 |
| Albumin (by every 1 g/dL) | 0.49 (0.28–0.83) | 0.009 |
| Pre-ALT (by every 40 IU/L) | 0.85 (0.72–1.01) | 0.057 |
| Pre-AFP (by every 10 ng/mL) | 1.00 (0.99–1.02) | 0.683 |
| HCV genotype, 1 / 2 | 0.88 (0.58–1.33) | 0.536 |
| rs17047200, AT+TT / AA | 1.60 (1.06–2.42) | 0.026 |
| Body mass index, (by every 1 unit) | 1.02 (0.95–1.10) | 0.549 |
| Diabetes, + / − | 1.78 (1.08–2.94) | 0.023 |
| Anti-HBc, + / − | 1.23 (0.82–1.85) | 0.323 |
| Post-ALT, by every 40 IU/L | 0.99 (0.69–1.42) | 0.965 |
| Post-AFP, by every 10 ng/mL | 1.88 (1.40–2.51) | <0.001 |
| Multivariate Analysis | | |
| Albumin (by every 1 g/dL) | 0.43 (0.25–0.76) | 0.004 |
| rs17047200, AT+TT / AA | 1.86 (1.12–3.09) | 0.017 |
| Post-AFP, by every 10 ng/mL | 1.90 (1.37–2.65) | <0.001 |

*Fig. 12*

|  |  |  | Genotype | | | Allele | |
| --- | --- | --- | --- | --- | --- | --- | --- |
| Population | Ethnicity | n | AA | AT | TT | A | T |
| The present study | Japanese | 941 | 0.772 | 0.211 | 0.017 | 0.877 | 0.123 |
| HapMap-JPT | Japanese | 112 | 0.813 | 0.179 | 0.009 | 0.902 | 0.098 |
| HapMap-CHB | Chinese | 136 | 0.816 | 0.169 | 0.015 | 0.901 | 0.099 |
| HapMap-CHD | Chinese | 109 | 0.789 | 0.193 | 0.018 | 0.885 | 0.115 |
| HapMap-CEU | European | 112 | 0.759 | 0.205 | 0.036 | 0.862 | 0.138 |
| HapMap-TSI | European | 102 | 0.784 | 0.206 | 0.010 | 0.887 | 0.113 |
| HapMap-GIH | Indians | 101 | 0.792 | 0.188 | 0.020 | 0.886 | 0.114 |
| HapMap-MEX | Mexican | - | - | - | - | - | - |
| HapMap-ASW | African | 57 | 0.509 | 0.439 | 0.053 | 0.728 | 0.272 |
| HapMap-LWK | African | 110 | 0.645 | 0.345 | 0.009 | 0.818 | 0.182 |
| HapMap-MKK | African | 155 | 0.716 | 0.271 | 0.013 | 0.852 | 0.148 |
| HapMap-YRI | African | 147 | 0.456 | 0.429 | 0.116 | 0.670 | 0.330 |

*Fig. 13*

```
                              SEQUENCE LISTING

<160> NUMBER OF SEQ ID NOS: 10

<210> SEQ ID NO 1
<211> LENGTH: 1001
<212> TYPE: DNA
<213> ORGANISM: Homo sapiens

<400> SEQUENCE: 1
aaagttgaat taaaagcatt accaaaccaa tcagcatgtt aaattggcaa agaattgttt      60
aatgaaaatt ggatatttat aagctaaata ggttatttag cagttctgtt aaaatgtcac     120
aatctaggcg acttgtgctt tatactgtgt attttctact gctcaagtac aacttacact     180
caaaaattga tattactaaa tgaattgtca ataacaaat tagaaagata ttttacctca      240
tataatttag aattatagtt catcactcat taaccctaaa attatgtcat taatgactta     300
aagctacttt taaagaatgc aataaatttg ggttttgatc tacttcattc taaagatgat     360
gtcatcaagc aaatagttcc caggtaagga atttggaact gttaaaccat tgaattcacc     420 ccttttttcca tttatgccca ttttatgctc gtatgtcatt tcaactcttt ttttttttg     480 cccacttatg tccatttcac wgttcattga catctatttc tgaaggcaag gtcaggaaaa     540
gggaaaaata ttcaaatgta ttaagctgct tttataaaac tttcttggta aaaagtagag     600
aagggtgtgt aaatgaaacc ttaatacttg gacacattta ttaattaccc atttttcca     660 aaccaaagtt tattattaa aaatttgtg ttaactgtat ttttaaaatt atgcttttct       720
aaagtacatt atttatagac atacgcattc atttgttaaa atataattaa ctgtccaaat    780
gtttattttt tctagaatat gaatttaagt tttgatagaa ataacatgct cagtaatttg    840
acctgaaatt aatcataaag agttacagaa ttttatttc tggtaaatgc ttggaatgga     900
gttttccata aaacatttaa caaatggata tttaggttcc agttcagtca aagtgcctct    960
cttctgctac tgagttatat tgtttagaac taacctgagt t                        1001

<210> SEQ ID NO 2
<211> LENGTH: 40
```

```
<212> TYPE: DNA
<213> ORGANISM: Homo sapiens

<400> SEQUENCE: 2
aactccattc caagcattta ccagaaaata aaattctgta                    40

<210> SEQ ID NO 3
<211> LENGTH: 44
<212> TYPE: DNA
<213> ORGANISM: Homo sapiens

<400> SEQUENCE: 3
acctcatata atttagaatt atagttcatc actcattaac ccta               44

<210> SEQ ID NO 4
<211> LENGTH: 28
<212> TYPE: DNA
<213> ORGANISM: Homo sapiens

<400> SEQUENCE: 4
catcttcaga aatagatgtc aatgtaca                                 28

<210> SEQ ID NO 5
<211> LENGTH: 46
<212> TYPE: DNA
<213> ORGANISM: Homo sapiens

<400> SEQUENCE: 5
ccgtgtccac tctagaaaaa ccttcagaaa tagatgtcaa tgtact             46

<210> SEQ ID NO 6
<211> LENGTH: 61
<212> TYPE: DNA
<213> ORGANISM: Homo sapiens

<400> SEQUENCE: 6
gtgaaatgga cataagtggg caaaaaaaaa aaagagttca tggacgtaat gtaagtgagc   60
a                                                                  61

<210> SEQ ID NO 7
<211> LENGTH: 26
<212> TYPE: DNA
<213> ORGANISM: Homo sapiens

<400> SEQUENCE: 7
gctcgtatgt catttcaact cttttt                                  26

<210> SEQ ID NO 8
<211> LENGTH: 23
<212> TYPE: DNA
<213> ORGANISM: Homo sapiens

<400> SEQUENCE: 8
cctgaccttg ccttcagaaa tag                                     23

<210> SEQ ID NO 9
<211> LENGTH: 17
<212> TYPE: DNA
<213> ORGANISM: Homo sapiens

<400> SEQUENCE: 9
ccatttcaca gttcatt                                            17
```

```
<210> SEQ ID NO 10
<211> LENGTH: 17
<212> TYPE: DNA
<213> ORGANISM: Homo sapiens

<400> SEQUENCE: 10
tccatttcac tgttcat                                                    17
```

PREDICTION OF HEPATOCELLULAR CARCINOMA ONSET AFTER CLEARANCE OF HEPATITIS C VIRUS

TECHNICAL FIELD

The present invention relates to the prediction of the development of hepatocellular carcinoma (HCC) after hepatitis C virus (HCV) eradication. Specifically, the present invention relates to a predictive marker for the development of HCC after HCV eradication and uses thereof (for example, a method for examining the risk of developing HCC after HCV eradication). This application claims priority to Japanese Patent Application No. 2016-093483, filed on May 6, 2016, the entire contents of which are hereby incorporated by reference.

BACKGROUND ART

Chronic hepatitis C virus (HCV) infection is responsible for the progression of hepatic fibrosis, which in turn leads to liver cirrhosis and hepatocellular carcinoma in a course of time of 20 to 30 years. At worldwide levels, near 30% of patients with liver cirrhosis and hepatocellular carcinoma are attributable to HCV infection, and it has been reported that about 500,000 people died therefrom in 2010 (Non-Patent Literature 1). It is estimated that in the United States, HCV-related liver cirrhosis and hepatocellular carcinoma is increasing until 2020, and the number of deaths therefrom is continued to increase until 2022 (Non-Patent Literature 2). In recent years, dramatic progress in the treatment for HCV infection, combinations of interferon-free direct-acting antiviral agents which have been employed in the past, achieve a sustained virological response of more than 90%, and make it possible to result in comparable therapeutic effects also in refractory patients with liver cirrhosis (Non-Patent Literature 3). However, it has been reported that even when such treatments can accomplish the eradication of HCV in patients with HCV infection, the risk of carcinogenesis does not completely disappear, and the cumulative incidence of carcinogenesis at 5 years after HCV eradication is 2.3 to 8.8% (Non-Patent Literature 4). Therefore, the prevention of and surveillance for carcinogenesis after HCV eradication are very important issues in the future when antiviral agents can yield sustained virological response.

CITATION LIST

Non Patent Literature

[PTL 1] Lozano R, Naghavi M, Foreman K, et al., Global and regional mortality from 235 causes of death for 20 age groups in 1990 and 2010: a systematic analysis for the Global Burden of Disease Study 2010. Lancet 2012; 380:2095-128.

[PTL 2] Davis G L, Alter M J, El-Serag H, et al., Aging of hepatitis C virus (HCV)-infected persons in the United States: a multiple cohort model of HCV prevalence and disease progression. Gastroenterology 2010; 138:513-21, 521 e1-6.

[PTL 3] Reddy K R, Bourliere M, Sulkowski M, et al., Ledipasvir and sofosbuvir in patients with genotype 1 hepatitis C virus infection and compensated cirrhosis: An integrated safety and efficacy analysis. Hepatology 2015; 62:79-86.

[PTL 4] Hiramatsu N, Oze T, Takehara T., Suppression of hepatocellular carcinoma development in hepatitis C patients given interferon-based antiviral therapy. Hepatol Res 2014; 45:152-61.

[PTL 5] Makiyama A, Itoh Y, Kasahara A, et al., Characteristics of patients with chronic hepatitis C who develop hepatocellular carcinoma after a sustained response to interferon therapy. Cancer 2004; 101:1616-22.

[PTL 6] Chang K C, Hung C H, Lu S N, et al., A novel predictive score for hepatocellular carcinoma development in patients with chronic hepatitis C after sustained response to pegylated interferon and ribavirin combination therapy. J Antimicrob Chemother 2012; 67:2766-72.

[PTL 7] Sato A, Sata M, Ikeda K, et al., Clinical characteristics of patients who developed hepatocellular carcinoma after hepatitis C virus eradication with interferon therapy: current status in Japan. Inter Med 2013; 52:2701-6.

[PTL 8] Arase Y, Kobayashi M, Suzuki F, et al., Effect of type 2 diabetes on risk for malignancies included hepatocellular carcinoma in chronic hepatitis C. Hepatology 2013; 57:964-73.

[PTL 9] Matsuura K, Watanabe T, Tanaka Y., Role of IL28B for chronic hepatitis C treatment toward personalized medicine. J Gastroenterol Hepatol 2014; 29:241-9.

[PTL 10] Matsuura K, Tanaka Y., Host genetic variants influencing the clinical course of hepatitis C virus infection. J Med Virol 2016; 88:185-95.

[PTL 11] Prokunina-Olsson L, Muchmore B, Tang W, et al., A variant upstream of IFNL3 (IL28B) creating a new interferon gene IFNL4 is associated with impaired clearance of hepatitis C virus. Nat Genet 2013; 45:164-71.

[PTL 12] Rauch A, Kutalik Z, Descombes P, et al., Genetic variation in IL28B is associated with chronic hepatitis C and treatment failure: a genome-wide association study. Gastroenterology 2010; 138:1338-45, 1345 e1-7.

[PTL 13] Thomas D L, Thio C L, Martin M P, et al., Genetic variation in IL28B and spontaneous clearance of hepatitis C virus. Nature 2009; 461:798-801.

[PTL 14] Fellay J, Thompson A J, Ge D, et al., ITPA gene variants protect against anaemia in patients treated for chronic hepatitis C. Nature 2010; 464:405-8.

[PTL 15] Tanaka Y, Kurosaki M, Nishida N, et al., Genome-wide association study identified ITPA/DDRGK1 variants reflecting thrombocytopenia in pegylated interferon and ribavirin therapy for chronic hepatitis C. Hum Mol Genet 2011; 20:3507-16.

[PTL 16] Iio E, Matsuura K, Nishida N, et al., Genome-wide association study identifying a PSMD3 variant associated with neutropenia in interferon-based therapy for chronic hepatitis C. Hum Genet 2015; 134:279-89.

[PTL 17] Patin E, Kutalik Z, Guergnon J, et al., Genome-wide association study identifying variants associated with progression of liver fibrosis from HCV infection. Gastroenterology 2012; 143:1244-52 e1-12.

[PTL 18] Urabe Y, Ochi H, Kato N, et al., A genome-wide association study of HCV-induced liver cirrhosis in the Japanese population identifies novel susceptibility loci at the MHC region. J Hepatol 2013; 58:875-82.

[PTL 19] Kumar V, Kato N, Urabe Y, et al., Genome-wide association study identifying a susceptibility locus for HCV-induced hepatocellular carcinoma. Nat Genet 2011; 43:455-8.

[PTL 20] Miki D, Ochi H, Hayes C N, et al., Variation in the DEPDC5 locus is associated with progression to hepatocellular carcinoma in chronic hepatitis C virus carriers. Nat Genet 2011; 43: 797-800.

[PTL 21] Nishida N, Tanabe T, Takasu M, et al., Further development of multiplex single nucleotide polymorphism typing method, the DigiTag2 assay. Anal Biochem 2007; 364:78-85.

[PTL 22] Berry R, Jowitt T A, Garrigue-Antar L, et al., Structural and functional evidence for a substrate exclusion mechanism in mammalian tolloid like-1 (TLL-1) proteinase. FEBS Lett 2010; 584:657-61.

SUMMARY OF INVENTION

Technical Problem

With regard to the prediction of the development of hepatocellular carcinoma (HCC) after the eradication of hepatitis C virus (HCV) with treatment regimens, there are reported, as risk factors, older age, male sex, advanced hepatic fibrosis, alcohol drinking, complicating diabetes, and blood test findings such as platelet count, lower albumin level, and higher α-fetoprotein level (Non-Patent Literatures 5 to 8). However, a sufficient prediction of the development of HCC after HCV eradication cannot be made even when these previously reported risk factors are used. Thus, there is a desire to develop a new predictive marker of carcinogenesis after HCV eradication. On the other hand, in these days when improvements in therapeutic treatments make it possible to achieve the eradication of HCV virus in most patients with HCV infection, a most important issue after the HCV virus eradication is surveillance for carcinogenesis, and there is an earnest desire to provide a new predictive marker that can solve this issue.

Solution to Problem

To date, there is reported no comprehensive examination over all of the host genes involved in the development of HCC after HCV eradication. In the course of the investigation to solve the above-mentioned issues, the present inventors focused on host genetic factors and aimed to find a risk factor related to the development of HCC after HCV eradication. Specifically, the present inventors conducted a genome-wide association study (GWAS) by typing single nucleotide polymorphisms (SNPs) in 457 Japanese patients who the eradication of HCV had been achieved with anti-HCV treatment (one patient was excluded from the subsequent analysis due to poor typing results) and classifying them into a carcinogenic group and a non-carcinogenic group. A plurality of selected candidate SNPs was subjected to replication study using these independent carcinogenic and noncarcinogenic groups, with the result that a minor allele of rs17047200, a SNP which is present in the intron region within the TLL1 (tolloid-like protein 1) gene located on chromosome 4, was identified to be associated with carcinogenesis. When examined using a combination of the results from the GWAS and the validation study, this SNP was found to show an odds ratio=2.37 (P=2.66×10$^{-8}$) and to satisfy the significance level of the genome-wide association study (P value <5×10$^{-8}$). In addition, it was found that patients with a minor genotype of rs17047200 (carrying the risk allele) among the patients under study tended to have a significantly higher cumulative incidence of carcinogenesis, relative to those with a major genotype (carrying no risk allele) (log rank test: P<0.001). Furthermore, when a multivariate analysis was made including other previously reported risk factors, the rs17047200 gene polymorphism was identified to be an independent risk factor for the development of HCC after HCV eradication (hazard ratio=1.78, P=0.008). The present inventors also paid attention to the fact that advanced hepatic fibrosis was reported to be a major risk factor related to the development of HCC after HCV eradication, and divided the patients into a group of advanced fibrosis and a group of mild fibrosis to make further analysis, leading to the success in the construction of different predictive models for carcinogenesis including the rs17047200 genotype in both groups.

As described above, the present inventors were successful, by their original examination, in identifying a SNP that is extremely useful in predicting the development of HCC after HCV eradication. If this SNP is used as a predictive marker of HCC after HCV eradication, then it is possible to narrow down patients who are highly likely to develop HCC after HCV eradication, that is, a high-risk group. It should be noted that the SNP, successfully identified by the present inventors, is an independent predictive marker, and by combining it with the previously reported risk factors, it is possible to make a more clear assessment of the (degree of) risk of developing HCC after HCV eradication. In fact, the present inventors were also successful in constructing a highly useful predictive model of carcinogenesis, which combines the SNPs successfully identified by the present inventors and the previously reported risk factors.

Based on the above results and discussion, the following inventions are provided.

[1] A method for examining a risk of developing hepatocellular carcinoma after hepatitis C virus eradication, characterized by detecting, in a nucleic acid sample collected from a subject, a single nucleotide polymorphism identified by the accession number rs17047200 in a SNP database at the National Center for Biotechnology Information (NCBI).

[2] The risk examination method according to [1], characterized by assessing the risk according to any of the following criteria:

(a) the subject is at high risk if an allele with T as the single nucleotide polymorphic base is detected;

(b) the risk is in the following order: risk in the case of type AA<risk in the case of type AT, risk in the case of type TT;

(c) the risk is in the following order: risk in the case of type AA<risk in the case of type AT<risk in the case of type TT.

[3] The risk examination method according to [1] or [2], characterized in that the risk of developing hepatocellular carcinoma is assessed in combination of the single nucleotide polymorphism and one or more risk factors selected from the group consisting of older age, male sex, lower platelet count, advanced hepatic fibrosis, higher ALT level, higher α-fetoprotein level, higher γ-GTP level, lower albumin level, and complicating diabetes.

[4] The risk examination method according to [3], comprising an assessment procedure consisting of the following:

(i) a step of classifying the subject according to a stage of hepatic fibrosis, and (ii) a step of further classifying the subject in combination of the single nucleotide polymorphism and one or more risk factors selected from the group consisting of older age, male sex, lower platelet count, higher ALT level, higher α-fetoprotein level, higher γ-GTP level, lower albumin level, and complicating diabetes, thereby to assess the subject for the risk.

[5] The risk examination method according to [4], wherein in step (i), Group 1 with the stage of hepatic fibrosis being stages 0 to 2 and Group 2 with the stage of hepatic fibrosis being stages 3 to 4 are defined, and when the subject is classified into the Group 1, the subject is further classified in combination of the single nucleotide polymorphism and as the risk factor, older age, thereby to assess the subject for the risk, or when the subject is classified into the Group 2, the subject is further classified in combination of the single nucleotide polymorphism, and as the risk factors, lower albumin level and higher α-fetoprotein level, thereby to assess the subject for the risk.

[6] The risk examination method according to any one of [1] to [5], comprising the following:

(I) a step of deciding or modifying a treatment regimen for the subject, based on the assessment result.

[7] A reagent for examining a risk of developing hepatocellular carcinoma after hepatitis C virus eradication, comprising a nucleic acid for detecting a single nucleotide polymorphism identified by the accession number rs17047200 in a SNP database at the National Center for Biotechnology Information (NCBI), wherein the nucleic acid comprises a complementary sequence to a given region comprising the polymorphism site and specifically hybridizes thereto.

[8] A kit for examining a risk of developing hepatocellular carcinoma after hepatitis C virus eradication, comprising the reagent according to [7].

[9] A predictive marker for hepatocellular carcinoma development after hepatitis C virus eradication, composed of a single nucleotide polymorphism identified by the accession number rs17047200 in a SNP database at the National Center for Biotechnology Information (NCBI).

BRIEF DESCRIPTION OF DRAWINGS

FIG. 2: Summary of patients' background. Data are expressed in numerical values for category data or median values (first-third quartiles) for non-categorical data. GWAS, genome-wide association study; CTRL, control; ALT, alanine aminotransaminase; γ-GTP, γ-glutamyl transpeptidase; APRI, aspartate aminotransferase (AST)-to-platelet ratio index; FIB-4, fibrosis-4; HCV, hepatitis C virus; N.A., not available; PEG-IFN, pegylated interferon; IFN mono, interferon monotherapy; RBV, ribavirin; PI, protease inhibitor; HCC, hepatocellular carcinoma.

FIG. 3: Primers and probes for rs17047200 typing designed in the DigiTag2 assay. The base t (lower case) in the query probe sequences represents a mismatched base.

FIG. 4: Primers and probes for rs17047200 typing designed in the TaqMan® assay. VIC® and FAM™ are fluorescent dyes with which the respective probes are labeled.

FIG. 7: TLL1 SNP associated with the development of hepatocellular carcinoma after HCV eradication. The numbers of rs17047200 types, 11 (TT), 12 (TA), and 22 (AA), in the Case group and the Control group of the GWAS and the replication study are indicated. The OR and P values were calculated by comparing the frequencies of T- and A- alleles (chi-square test). (b) The allele distributions from the GWAS and the replication study (a) were combined. SNP, single nucleotide polymorphism; HCC, hepatocellular carcinoma; HCV, hepatitis C virus; GWAS, genome-wide association study; Chr, chromosome; CTRL, control; CI, confidence interval.

FIG. 9: Multivariate analysis of factors associated with the development of hepatocellular carcinoma after HCV eradication. Taking univariate analysis results and confounding factors into account, the multivariate analysis was performed in which sex, age, γ-GTP level, albumin level, pre-treatment AFP level, hepatic fibrosis progression, rs17047200 genotype, the presence or absence of complicating diabetes, the presence or absence of HBc antibody, post-treatment ALT level, and post-treatment AFP level were used as covariates. HCC, hepatocellular carcinoma; HCV, hepatitis C virus; HR, hazard ratio; CI, confidence interval; γ-GTP, γ-glutamyl transpeptidase; Pre, pre-treatment; ALT, alanine aminotransaminase; AFP, α-fetoprotein; Post, post-treatment (24 weeks after the end of treatment).

FIG. 10: Multivariate analysis of factors associated with the development of hepatocellular carcinoma after HCV eradication in patients with mild hepatic fibrosis (at stages F0 (n=12), F1 (n =136), and F2 (n=93)). Only patients with a platelet count $\geq 130 \times 10^9$/L and an albumin level >4.0 g/dL were subjected to the analysis. Taking univariate analysis results and confounding factors into account, the multivariate analysis was performed in which sex, age, pre-treatment AFP level, rs17047200 genotype, and the presence or absence of HBc antibody were used as covariates. HCC, hepatocellular carcinoma; HCV, hepatitis C virus; HR, hazard ratio; CI, confidence interval; γ-GTP, γ-glutamyl transpeptidase; Pre, pre-treatment; ALT, alanine aminotransaminase; AFP, α-fetoprotein; Post, post-treatment (24 weeks after the end of treatment).

FIG. 12: Multivariate analysis of factors associated with the development of hepatocellular carcinoma after HCV eradication in patients with advanced hepatic fibrosis (F3 (n=144) and F4 (n =82)). Taking univariate analysis results and confounding factors into account, the multivariate analysis was performed in which age, platelet count, γ-GTP level, albumin level, rs17047200 genotype, the presence or absence of complicating diabetes, and post-treatment AFP level were used as covariates. HCC, hepatocellular carcinoma; HCV, hepatitis C virus; HR, hazard ratio; CI, confidence interval; γ-GTP, γ-glutamyl transpeptidase; Pre, pre-treatment; ALT, alanine aminotransaminase; AFP, α-fetoprotein; Post, post-treatment (24 weeks after the end of treatment).

FIG. 13: Comparison of genotype and allele frequency of rs17047200 among ethnic groups. HapMap data was obtained from the website (http://hapmap.ncbi.nlm.nih.gov/index.html.en). JPT, Japanese in Tokyo, Japan; CHB, Han Chinese in Beijing, China; CHD, Chinese in Metropolitan Denver, Colo.; CEU, Utah residents with Northern and Western European ancestry; TSI, Toscans in Italy; GIH, Gujarati Indians in Houston, Tex.; MEX, Mexican residents in Los Angeles; ASW, African residents in Southwest USA; LWK, Luhya in Webuye, Kenya; MKK, Maasai in Kinyawa, Kenya; YRI, Yoruba in Ibadan, Nigeria.

DESCRIPTION OF EMBODIMENTS

1. Risk Examination Methods

Figure 1:
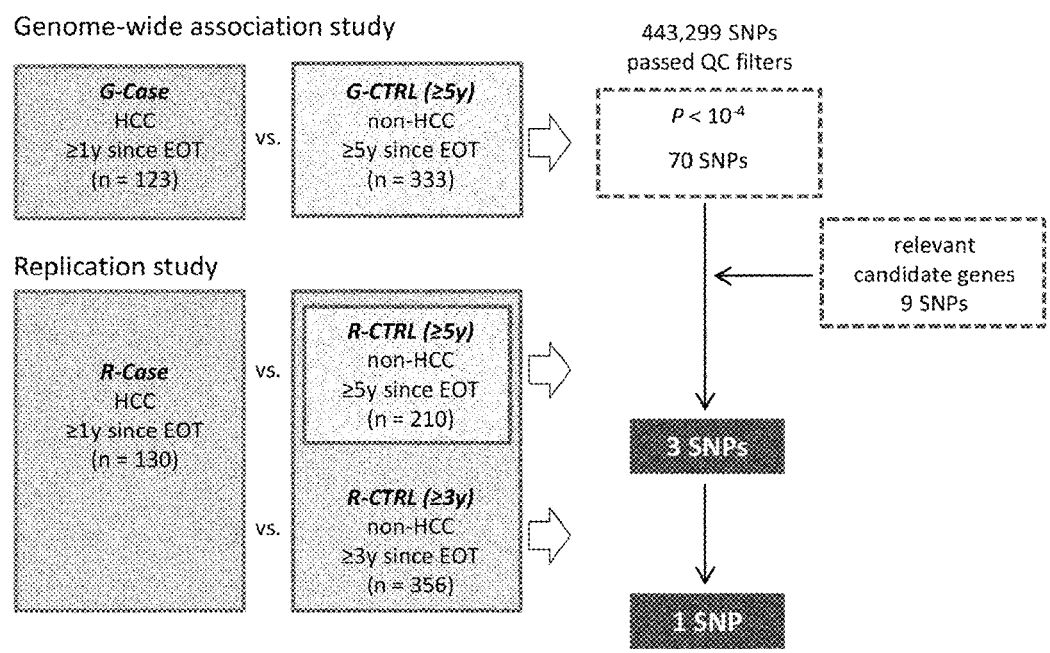
FIG. 1: Outline of the study design. HCC, hepatocellular carcinoma; EOT, end of treatment; CTRL, control; SNP, single nucleotide polymorphism; QC, quality control.

A first aspect of the present invention relates to a method for examining a risk of developing hepatocellular carcinoma after hepatitis C virus eradication. In the present invention, the "risk of developing hepatocellular carcinoma" refers to the degree of risk (possibility) of a subject developing hepatocellular carcinoma in the future. In the present invention, by "after hepatitis C virus eradication" is meant that by means of prior treatment, a sustained virological response (SVR) has been achieved with respect to hepatitis C virus. Therefore, in the risk examination method of the present invention, a patient who has received treatment for hepatitis C is a subject. SVR is defined as blood levels of HCV RNA below the detection sensitivity at 24 weeks after the end of treatment. The type of the prior treatment is not limited particularly, and examples thereof include, for example, interferon (IFN) therapies (using IFNα, PEGylated IFNα, and IFNβ), treatments with antiviral agents, and combination therapies of interferon and antiviral agents. As antiviral agents, use is made of purine nucleoside analogs (for example, ribavirin), NS3/4A protease inhibitors (for example, telabrevir, asunaprevir), NS5A inhibitors (daslatasvir, ledipasvir), NS5B polymerase inhibitors (sofosbuvir), and others.

In the risk examination method of the present invention, a single nucleotide polymorphism (SNP) identified by rs17047200 is detected and the risk is assessed and evaluated based on the detection result. That is, the present invention uses rs17047200 as a predictive marker in the risk assessment. Rs17047200 is a SNP which is present in the intron region within the TLL1 gene located on chromosome 4. TLL1 belongs to a family of BMP1/TLD-like proteinases. The rs number is an accession number in the SNP database at the National Center for Biotechnology Information (NCBI). The sequence of a genomic region containing the rs17047200 polymorphism position is shown in SEQ ID NO: 1, wherein the base at the position of the rs17047200 polymorphism is represented by W (A or T).

In the present invention, the term "detecting a single nucleotide polymorphism" can be replaced with the term "analyzing a single nucleotide polymorphism." Detection of a single nucleotide polymorphism (SNP) reveals the state (i.e., the kind of the base) at the position of the polymorphism.

In place of the rs17047200 polymorphism, or in combination with the rs17047200 polymorphism, a SNP in strong linkage disequilibrium with the rs17047200 polymorphism may be a target to be detected. The reason is that a SNP in strong linkage disequilibrium with a given particular SNP ($R^2$ value >0.8) behaves in a similar way to it, and thus would be useful as a predictive marker for carcinogenesis as in the case of the rs17047200 polymorphism. SNPs in strong linkage disequilibrium with rs17047200 can be identified using analysis software, such as Haploview and ARLEQUIN.

In implementing the risk examination method of the present invention, a nucleic acid sample collected from a subject is first prepared. The present invention uses a nucleic acid sample derived from a person (subject) in need of assessing the risk of developing hepatocellular carcinoma after hepatitis C virus eradication. The nucleic acid sample can be prepared from blood, saliva, lymph, urine, perspiration, skin cells, mucosal cells, hair, or the like of the subject using known extraction and purification methods. Genomic DNA of any length may be used as the nucleic acid sample, as long as it contains the polymorphism site to be detected.

The scope of application of the present invention is not limited to Japanese individuals. This means that the present invention is also applicable to Mongoloids and other ethnic groups (Caucasoid, etc.) other than Japanese individuals. However, in light of the fact that ethnic populations who are genetically relative (for example, Chinese and Korean populations are genetically close to the Japanese population) often have similar tendencies with respect to the type and frequency of polymorphisms, and of the results obtained from the comparison of the genotype and allele frequency of the rs17047200 polymorphism among various ethnic groups (see Examples below and FIG. 13), the subject in the present invention is preferably Mongoloid (Japanese, Chinese, Korean, etc.) or Caucasoid, further preferably Mongoloid, and even more preferably Japanese.

Methods for detecting (analyzing) the polymorphism are not limited particularly, and known methods can be employed, including for example, methods by which allele-specific primers (or probes) are used to detect the presence or absence of amplification and the polymorphism in amplification products by PCR method, by means of fluorescence or luminescence; PCR-RFLP (restriction fragment length polymorphism) methods using PCR (polymerase chain reaction) method; PCR-SSCP (single strand conformation polymorphism) methods (for example, Orita, M. et al., Proc. Natl. Acad. Sci., U.S.A., 86, 2766-2770 (1989)); PCR-SSO (specific sequence oligonucleotide) methods; ASO (allele specific oligonucleotide) hybridization methods combining PCR-SSO and dot-hybridization methods (for example, Saiki, Nature, 324, 163-166 (1986)); TaqMan® (Roche Molecular Systems, Inc.)-PCR methods (Livak, K J, Genet Anal, 14, 143 (1999); Morris, T. et al., J. Clin. Microbiol., 34, 2933 (1996)); Invader® (Third Wave Technologies Inc.) methods (Lyamichev V et al., Nat Biotechnol, 17, 292 (1999)), methods using FRET (Fluorescence Resonance Energy Transfer) (for example, Heller, Academic Press Inc., pp. 245-256 (1985); Cardullo et al., Proc. Natl. Acad. Sci. USA, 85, 8790-8794 (1988); WO 99/28500; JP 2004-121232 A); ASP-PCR (Allele Specific Primer-PCR) methods (for example, WO 01/042498); MALDI-TOF/MS (matrix) methods using primer extension method (Haff L A, Smirnov I P, Genome Res 7, 378 (1997)); RCA (rolling cycle amplification) methods (Lizardi P M et al., Nat Genet 19, 225 (1998)); methods using DNA chips or microarrays (for example, Wang D G et al., Science 280, 1077 (1998)); primer extension methods; southern blot hybridization methods; dot hybridization methods (Southern, E., J. Mol. Biol. 98, 503-517 (1975)); and DigiTag2 method (see Nishida N, Tanabe T, Takasu M, et al., Further development of multiplex single nucleotide polymorphism typing method, the DigiTag2 assay. Anal Biochem 2007; 364:78-85). Further, the polymorphism site to be detected may be subjected to direct sequencing. Any combination of these methods may be used to detect the polymorphism. In addition, it is also possible that a nucleic acid sample (or alternatively a partial region of a nucleic acid sample) is amplified in advance using a nucleic acid amplification method such as PCR method or PCR-derived method, and then submitted to any of the above-mentioned detection methods.

In cases when the detection of the polymorphism is performed using a large number of nucleic acid samples, it is particularly preferable to employ a detection method by which detection can be made for many samples in a relatively short time, such as an allele-specific PCR method, an allele-specific hybridization method, a TaqMan®-PCR method, an Invader method, a method using FRET, an ASP-PCR method, a MALDI-TOF/MS (matrix) method using a primer extension method, a RCA (rolling cycle amplification) method, or a method using DNA chips or microarrays, or DigiTag2 method.

The above-described methods use nucleic acids corresponding to the respective methods, such as probes and primers, which are also referred to as "polymorphism detection nucleic acids" in the present invention. An example of a polymorphism detection nucleic acid that is used as a probe can be a nucleic acid which specifically hybridizes to a chromosomal region (partial chromosomal region) including the polymorphism position to be detected. The length of such a "partial chromosome region" in this case is, for example, 16 to 500 bases long, preferably 18 to 200 bases long. In addition, while the nucleic acid preferably has a sequence complementary to the partial chromosomal region, it may have some mismatches, as long as they do not prevent its specific hybridization. The number of mismatches is 1 to several, preferably 1 to 5, further preferably 1 to 3. Here, by the term "specific hybridization" is meant that under hybridization conditions (preferably stringent conditions) that are usually employed in the detection with a nucleic acid probe, the probe results in hybridization to the target nucleic acid (partial chromosomal region) and at the same time, no significant cross-hybridization with other nucleic acids. A person skilled in the art would be easily able to set hybridization conditions, for example, with reference to Molecular Cloning (Third Edition, Cold Spring Harbor Laboratory Press, New York).

An example of a polymorphism detection nucleic acid that is used as a primer can be a nucleic acid that has a sequence complementary to a certain region (a certain chromosomal region) including the polymorphism position to be detected and is designed so as to allow specific amplification of a DNA fragment including the polymorphism portion. Another example of a polymorphism detection nucleic acid that is used as a primer can be a set of nucleic acids that are designed so that only when the polymorphism site to be detected is located on a risk allele, they allow specific amplification of a DNA fragment comprising the polymorphism site. A more specific example of such a set of nucleic acids can be a set of nucleic acids that are designed so as to allow specific amplification of a DNA fragment comprising the polymorphism site to be detected, consisting of a sense primer that specifically hybridizes to a certain region (a certain chromosomal region) comprising the polymorphism site on the antisense strand, the polymorphism site being located on a risk allele, and an antisense primer that specifically hybridizes to a certain region on the sense strand (which is a region close to the polymorphism site). In these cases, the length of the DNA fragment amplified is set as appropriate in a range suitable for its detection, and is, for example, 15 to 1000 bases long, preferably 20 to 500 bases long, further preferably 30 to 200 bases long. As in the case of the probe, a polymorphism detection nucleic acid that is be used as a primer may also have some mismatches to a sequence that is a template, as long as it is capable of specifically hybridizing the sequence to be amplified (template) and amplifying the DNA fragment of interest. The number of mismatches is 1 to several, preferably 1 to 3, further preferably 1 to 2.

For the polymorphism detection nucleic acids (probes, primers), DNAs, RNAs, peptide nucleic acids (PNAs), and the like are used as appropriate, depending upon detection methods. The polymorphism detection nucleic acids have any nucleotide length allowing their function to be exerted, and by way of example, are 15 to 150 bases long, preferably 16 to 100 bases long when used as a probe. On the other hand, when used as a primer, the polymorphism detection nucleic acid is, by way of example, 10 to 70 bases long, preferably 15 to 60 bases long, further preferably 20 to 50 bases long.

The polymorphism detection nucleic acids (probes, primers) can be synthesized by known methods such as phosphodiester method. Regarding the design, synthesis, etc. of the polymorphism detection nucleic acids, reference can be made to books, for example, Molecular Cloning, Third Edition, Cold Spring Harbor Laboratory Press, New York; and Current Protocols in molecular biology (edited by Frederick M. Ausubel et al., 1987).

A polymorphism detection nucleic acid for use in the present invention may be labeled in advance with a labeling substance. The use of such a labeled nucleic acid allows one to detect the polymorphism, for example, by using the amount of labeling of the amplification product as an index. In addition, if two primers that are each designed to specifically amplify a partial DNA region in a gene corresponding to each of the genotypes related to the polymorphism are labeled with labeling substances that are different from each other, then the genotypes of the nucleic acid samples can be discriminated by means of the labeling substance detected from and the amount of labeling in the amplification product. A specific example of a detection method using such a labeled primer can be a method by which two nucleic acid primers (allele-specific sense primers) that each specifically hybridize to the sense strand comprising a region corresponding to each of the genotypes related to the polymorphism are each labeled with fluorescein isothiocyanate and Texas red, and these labeled primers and an antisense primer that specifically hybridizes to the antisense strand are used to amplify a partial DNA region comprising the polymorphism site, followed by measuring the amount of labeling of the respective fluorescent substances in the resulting amplification product, thereby to detect the polymorphism. In this case, if the antisense primer is labeled, for example, with biotin, then the amplification product can be separated using specific binding between biotin and avidin.

Examples of a labeling substance that is used for labeling the polymorphism detection nucleic acid can be fluorescent dyes, such as 7-AAD, Alexa Fluor® 488, Alexa Fluor® 350, Alexa Fluor® 546, Alexa Fluor® 555, Alexa Fluor® 568, Alexa Fluor® 594, Alexa Fluor® 633, Alexa Fluor® 647, Cy™2, DsRED, EGFP, EYFP, FITC, PerCP™, R-Phycoerythrin, Propidium Iodide, AMCA, DAPI, ECFP, Methyl-Coumarin, Allophycocyanin (APC), Cy™3, Cy™5, Rhodamine-123, Tetramethylrhodamine, Texas Red®, PE, PE-Cy™5, PE-Cy™5.5, PE-Cy™7, APC-Cy™7, Oregon Green, FAM™, VIC®, ABY®, carboxyfluorescein, carboxyfluorescein diacetate, and quantum dots; radioactive isotopes, such as $^{32}$P, $^{131}$I, and $^{125}$I; and biotin. Examples of a method for labeling the polymorphism detection nucleic acid can be a 5'-end labeling method using alkaline phosphatase and T4 polynucleotide kinase; a 3'-end labeling method using T4 DNA polymerase or Klenow fragment; a nick translation method; a random primer method (Molecular Cloning, Third Edition, Chapter 9, Cold Spring Harbor Laboratory Press, New York).

It is also possible to use an above-described polymorphism detection nucleic acid in a state where it is immobilized on an insoluble support. If an insoluble support that is to be used for immobilization is processed into chips, beads, or the like, then the detection of the polymorphism can more easily be carried out using the immobilized nucleic acid.

The following gives specific examples of primers and probes (Examples 1 and 2). Example 1 shows the primers and probes designed to be suitable for the DigiTag2 method. Example 2, on the other hand, shows the primers and probes designed to be suitable for TaqMan® assays.

Example 1

Forward primer:
(SEQ ID NO: 2)
5'-AACTCCATTCCAAGCATTTACCAGAAAATAAAATTCTGTA-3'

Reverse primer:
(SEQ ID NO: 3)
5'-ACCTCATATAATTTAGAATTATAGTTCATCACTCATTAACCCTA-3'

Query probe for major allele (A):
(SEQ ID NO: 4)
5'-ACCACCGCTTGAATACAAAACATCTTCAGAAATAGATGTCAATGtA
CA-3'

Query probe for minor allele (T):
(SEQ ID NO: 5)
5'-CCGTGTCCACTCTAGAAAAACCTTCAGAAATAGATGTCAATGtAC
T-3'

Common probe:
(SEQ ID NO: 6)
5'-GTGAAATGGACATAAGTGGGCAAAAAAAAAAAGAGTTCATGGACGT
AATGTAAGTGAGCA-3'

Example 2

Forward primer:
(SEQ ID NO: 7)
5'-GCTCGTATGTCATTTCAACTCTTTTT-3'

Reverse primer:
(SEQ ID NO: 8)
5'-CCTGACCTTGCCTTCAGAAATAG-3'

Probe for major allele (A):
(SEQ ID NO: 9)
5'-CCATTTCACAGTTCATT-3'

Probe for minor allele (T):
(SEQ ID NO: 10)
5'-TCCATTTCACTGTTCAT-3'

In the present invention, the risk is assessed on the basis of the detection result for the polymorphism, that is, the type of the allele detected or the combination (genotype) of the alleles detected. In this case, as is apparent from the criteria for the assessment of the polymorphism, the assessment can be made automatically/mechanically, even not on the basis of the judgment made by a person having expert knowledge, such as a doctor or a laboratory technician.

As shown in Examples which follow, it has been found that in the rs17047200 polymorphism, an allele having T (thymine) at the polymorphism site is a risk allele. Therefore, the assessment/evaluation of the risk is made, for example, according to the following criterion:

(a) the subject is at high risk if an allele with T as the polymorphic base is detected.

In a preferred embodiment of the present invention, the genotype (allele combination) is determined from the detection result for the polymorphism. Specifically, it is determined whether the allele combination is any of type AA (a homozygous allele combination in which the base at the polymorphism position is A), type AT (a heterozygous allele combination of an allele in which the base at the polymorphism position is A and an allele in which the base at the polymorphism position is T), and type TT (a homozygous allele combination in which the base at the polymorphism position is T). When these genotypes are used to assess the polymorphism, it is possible to make a more accurate assessment/evaluation. In the genotype-based risk assessment/evaluation, for example, the following criterion (b) or (c) can be employed.

(b) the risk is in the following order: risk in the case of type AA<risk in the case of type AT, risk in the case of type TT (c) the risk is in the following order: risk in the case of type AA<risk in the case of type AT<risk in the case of type TT In an embodiment of the present invention, the risk of developing hepatocellular carcinoma is assessed using the detection result for the rs17047200 polymorphism in combination with existing risk factors. The combination with existing risk factors leads to an improvement in the ability to predict the risk of developing hepatocellular carcinoma after hepatitis C virus eradication. The existing risk factors can be older age, male sex, lower platelet count, advanced hepatic fibrosis, higher ALT level, higher α-fetoprotein level, higher γ-GTP level, lower albumin level, and complicating diabetes. One or more of these risk factors are employed. Preferably, two or more risk factors are employed to achieve a further improvement in the ability to predict the risk.

Older age, usually an age of 60 years or above, represents a high risk (i.e., a risk factor) for carcinogenesis. Therefore, ages of 60 years or above can be employed as a risk factor for carcinogenesis. Lower platelet count usually represents a platelet count lower than that in the range of reference values (15 to $35 \times 10^4$/L). In particular, platelet counts less than $15 \times 10^4$/L represent a high risk (i.e., a risk factor) for carcinogenesis. Advanced hepatic fibrosis is represented by the stages of hepatic fibrosis (F stage). The F stages are classified into five stages: F0 (normal), F1 (mild fibrosis), F2 (moderate fibrosis), F3 (high-grade fibrosis), and F4 (liver cirrhosis). Usually, hepatic fibrosis at stage F3 or F4 is a risk factor for carcinogenesis after HCV eradication. Higher ALT level usually represents an ALT level higher than that in the range of reference values (10 to 42 U/L for males, 7 to 23 U/L for females). In particular, ALT levels higher than 42 U/L for males and 23 U/L for females represent a high risk (i.e., a risk factor) for carcinogenesis. Higher α-fetoprotein level usually represents an α-fetoprotein level higher than that in the range of reference values (10.0 ng/mL or less). In particular, α-fetoprotein levels higher than 10.0 ng/mL represent a high risk (i.e., a risk factor) for carcinogenesis. Higher γ-GTP level usually represents a γ-GTP levels higher than that in the range of reference values (13 to 64 U/L for males, 9 to 32 U/L for females). In particular, γ-GTP levels higher than 64 U/L for males and 32 U/L for females represent a high risk (i.e., a risk factor) for carcinogenesis. Lower albumin level usually represents an albumin level lower than that in the range of reference values (4.1 to 5.1 g/dL). In particular, albumin levels less than 4.1 g/dL represent a high risk (i.e., a risk factor) for carcinogenesis. Here, the respective numerical values regarding these risk factors are measurements obtained by blood test, that is, their blood concentrations or units calculated on the basis of their blood concentrations.

It is possible to identify not only patients at particularly high risk, but also patients at relatively high risk, using these risk factors with values that are relatively looser (for older age, for example, ages of 57 years or above; for lower platelet count, for example, platelet counts less than $20 \times 10^4$/L; for advanced hepatic fibrosis, for example, hepatic fibrosis at stages F2 to F4; for higher ALT level, for example, ALT levels higher than 35 U/L for males and 18 U/L for females; for higher α-fetoprotein level, for example, α-fetoprotein levels higher than 7 ng/mL; for higher γ-GTP level, for example, higher γ-GTP levels higher than 40 U/L for males and 25 U/L for females; and lower albumin level, for example, albumin levels less than 4.3 g/dL).

On the other hand, it is also possible to narrow down patients at particularly high risk, using these risk factors with values that are relatively stricter (for older age, for example, ages of 65 years or above; for lower platelet count, for example, platelet counts less than $12 \times 10^4$/L; for advanced hepatic fibrosis, for example, hepatic fibrosis at stage F4; for higher ALT level, for example, ALT levels higher than 50 U/L for males and 30 U/L for females; for higher α-fetoprotein level, for example, α-fetoprotein levels higher than 20 ng/mL; for higher γ-GTP level, for example, higher γ-GTP levels higher than 80 U/L for males and 50 U/L for females; and lower albumin level, for example, albumin levels less than 3.0 g/dL).

A subject carrying an above-described risk factor(s) (i.e., an above-described risk factor(s) being found in a subject) means that the subject is at high risk. Therefore, in general, it is meant that as a subject has an increasing number of risk factors, the risk becomes higher accordingly. The following shows a specific example of a set of risk groups that are defined when the risk is assessed according to the number of risk factors carried by a subject (wherein the risk groups are defined using the rs17047200 polymorphism and three risk factors).

Risk 1: rs17047200 polymorphism of type AA and no risk factors carried

Risk 2: rs17047200 polymorphism of type AT and one risk factor carried

Risk 3: rs17047200 polymorphism of type AT or TT and two risk factors carried

Risk 4: rs17047200 polymorphism of type AT or TT and three risk factors carried (wherein the degree of risk is: risk 1<risk 2<risk 3<risk 4.)

The risk factors may be different in the degree of significance or contribution in the risk assessment. Specifically, for example, among the above-mentioned risk factors, advanced hepatic fibrosis, older age, male sex, and rs17047200 polymorphisms of type AT or TT are of particular significance, and thus a subject carrying one or more of these risk factors is assessed to be at higher risk, relative to those carrying other risk factors than said risk factors.

In a preferred embodiment, a subject is submitted to a first-stage classification based on advanced hepatic fibrosis, followed by a second-stage classification using the rs17047200 polymorphism in combination with another risk factor(s), thereby to assess the subject for the risk. Accordingly, in this embodiment, the subject's risk is evaluated by an assessment procedure consisting of the following:

(i) a step of classifying the subject according to a stage of hepatic fibrosis, and (ii) a step of further classifying the subject in combination of the single nucleotide polymorphism and one or more risk factors selected from the group consisting of older age, male sex, lower platelet count, higher ALT level, higher α-fetoprotein level, higher γ-GTP level, lower albumin level, and complicating diabetes, thereby to assess the subject for the risk.

In step (i), the subject is classified on the basis of a stage of hepatic fibrosis. Accordingly, a plurality of groups related to fibrosis stages is defined, and the subject is classified into a corresponding group. By way of specific example, there are defined two groups, Group 1 with the stage of hepatic fibrosis being stages 0 to 2 and Group 2 with the stage of hepatic fibrosis being stages 3 to 4 are defined, and the subject is classified into a corresponding group. Such classification is followed by further classification of the subject in combination of the rs17047200 polymorphism and an above-mentioned risk factor(s). For example, when the subject has been classified into the Group 1, the subject is further classified in combination of the rs17047200 polymorphism, and older age as the risk factor, thereby to assess the subject for the risk. On the other hand, when the subject has been classified into the Group 2, the subject is further classified in combination of the rs17047200 polymorphism, and lower albumin level and higher α-fetoprotein level as the risk factor, the, thereby to assess the subject for the risk.

The assessment result is indicative of the risk of the subject developing hepatocellular carcinoma, and is useful for prevention and early detection of hepatocellular carcinoma. If a subject conducts preventive measures, improve lifestyle habits, or the like on the basis of the information that the subject is at high risk, then the subject's likelihood of developing (or suffering from) hepatocellular carcinoma can be reduced. The assessment result provides information that is also useful in the consideration of future treatment regimens. Therefore, in an embodiment of the present invention, the treatment regimen for the subject is determined or modified on the basis of the assessment result (step (I)). The treatment regimen for the subject is designed or selected, depending upon the subject's risk, which is based on the assessment result. Typically, a subject who has been classified into a high-risk group is recommended to undergo frequent and periodic medical examinations because early and aggressive therapeutic intervention is desired when a sign of the development of carcinogenesis is observed. In addition, it is desired to select a therapeutic treatment that makes allowance for the possibility of carcinogenesis in the future. On the other hand, when a subject has been classified into a low-risk group, for example, the frequency of periodic medical examinations can be reduced, leading to reduced burden on and medical costs of the patient. Note that when the present invention is practiced after the treatment is started or after the treatment regimen is decided, the assessment result can be used for modifying (reviewing) the treatment regimen.

2. Reagents and Kits for Risk Examination

Another aspect of the present invention provides a reagent and a kit for use in the examination of the risk of developing hepatocellular carcinoma after hepatitis C virus eradication. The reagent of the present invention consists of a nucleic acid (polymorphism detection nucleic acid) for detecting the rs17047200 polymorphism.

A polymorphism detection nucleic acid that is used as the reagent of the present invention, is designed as appropriate, depending upon the detection method to which it is applied, such as a method involving a PCR method using an above-mentioned allele-specific nucleic acid or the like; PCR-RFLP method; PCR-SSCP; TaqMan®-PCR method; Invader® method; and DigiTag2 method. Details on such a polymorphism detection nucleic acid are as described above, while the following shows specific examples of a polymorphism detection nucleic acid or a set of polymorphism detection nucleic acids that can be used as a component of the kit.

(1) an unlabeled or labeled nucleic acid having a sequence complementary to a chromosomal region (partial chromosomal region) where the base at the position of the polymorphism is A;

(2) an unlabeled or labeled nucleic acid having a sequence complementary to a chromosomal region (partial chromosomal region) where the base at the position of the polymorphism is T;

(3) a combination of the nucleic acids (1) and (2);

(4) a set of nucleic acids that are designed so as to allow specific amplification of a DNA fragment comprising the polymorphism site only when the base at the position of the polymorphism is A;

(5) a set of nucleic acids that are designed so as to allow specific amplification of a DNA fragment comprising the polymorphism site only when the base at the position of the polymorphism is T;

(6) a combination of the sets of nucleic acids (4) and (5); and (7) a set of nucleic acids that are designed so as to allow specific amplification of a DNA fragment including the polymorphism position, consisting of a sense primer that specifically hybridizes to a chromosomal region (a partial chromosomal region) including the polymorphism position at which the base is A, and/or a sense primer that specifically hybridizes to a chromosomal region (partial chromosomal region) including the polymorphism position at which the base is T, and an antisense primer that specifically hybridizes to a region close to the partial chromosomal region.

A kit of the present invention includes a reagent of the present invention, that is, a polymorphism detection nucleic acid of the present invention. The kit of the present invention may include reagents that are necessary in the use of the polymorphism detection nucleic acid, i.e., in the detection of the polymorphism, such as DNA polymerase, restriction enzyme(s), buffer solution, and chromogenic reagent; containers; instruments; and others. In general, the kit of the present invention is provided with an instruction manual.

EXAMPLES

In recent years, advances in large-scale single nucleotide polymorphism (SNP) analysis technology allow comprehensive analysis of the whole genome region, and genome-wide association studies (GWAS) are used to identify genetic polymorphisms involved in various multifactorial diseases in humans, for example, SNPs associated with effects, side effects, and natural history of interferon treatments in the field of HCV infection (Non-Patent Literatures 9 to 16). SNPs associated with advanced hepatic fibrosis and hepatocellular carcinoma in chronic hepatitis C patients have also been identified (Non-Patent Literatures 17 to 20). However, until now there has been reported no GWAS directed to the development of hepatocellular carcinoma after HCV eradication. Therefore, we conducted a GWAS to identify host factors related to the development of hepatocellular carcinoma after the eradication of HCV with interferon treatment in a Japanese population.

<Methods>

1. Patients

From 2007 through 2015, genomic DNA samples from 943 patients (457 patients for GWAS and 486 patients for the subsequent replication study) who had achieved HCV eradication with interferon-based therapy, and their clinical information were obtained from 43 facilities throughout Japan. In the GWAS, an association analysis was performed between two groups, a case group in which SNP typing results were obtained (G-Case, n=123), consisting of patients who had developed hepatocellular carcinoma at 1 year or more after the end of treatment, and a control group [G-CTRL ($\geq$5y), n=333], consisting of patients who had not developed hepatocellular carcinoma at 5 years or more after the end of treatment. In the replication study, on the other hand, an association analysis was performed on a case group (R-Case, n=130), consisting of patients who had developed hepatocellular carcinoma at 1 year or more after the end of treatment, and a control group [R-CTRL ($\geq$3 y), n=356], consisting of patients who had not developed hepatocellular carcinoma at 3 years or more after the end of treatment, including a stratified group of patients who had not developed hepatocellular carcinoma at 5 years or more after the end of treatment, [R-CTRL ($\geq$5y), n=210] (FIGS. 1 and 2).

2. SNP Typing

SNP typing in the GWAS was carried out using the Affymetrix Axiom Genome-Wide ASI 1 Array Plate (Affymetrix, Inc., Santa Clara, Calif.), and 443,299 SNPs satisfying a SNP call rate $\geq$95%, a minor allele frequency (MAF) $\geq$5%, and Hardy-Weinberg equilibrium (HWE) P$\geq$0.001 were subjected to an association analysis. SNP typing in the replication study was performed using the DigiTag2 assay (Nishida N, Tanabe T, Takasu M, et al., Further development of multiplex single nucleotide polymorphism typing method, the DigiTag2 assay. Anal Biochem 2007; 364:78-85) or the TaqMan® SNP Genotyping Assays (Applied Biosystems, Carlsbad, Calif.).

3. Statistical Analysis

The association between allele frequency of SNPs and carcinogenesis was analyzed in the GWAS and the replication study, using chi-square test. The genome wide level of significance after Bonferroni correction was set to P=1.12×$10^{-7}$ (0.05/443,299) for the GWAS and P=6.49×$10^{-4}$ (0.05/77) for the replication study, and the level of significance in the combined analysis was set to P<5×$10^{-8}$. Comparisons between two groups in other general analyses were performed using Mann-Whitney U-test, the cumulative incidence of carcinoma was analyzed by the Kaplan-Meier method, and a multivariate analysis of cumulative risk of carcinogenesis was performed using stepwise Cox proportional hazard model, with P<0.05 as a level of significance.

4. Establishment of the Method for Determining rs17047200 Genotype

The sequences of the primers and probes designed in the DigiTag2 assay which were used for SNP typing in the replication study are as shown in FIG. 3. The DigiTag2 method is a multiplex SNP typing method by which plural SNPs can be genotyped at a time using SNP-specific common probes that are each directed to a SNP to be analyzed and allele-specific query probes (Nishida N, Tanabe T, Takasu M, et al., Further development of multiplex single nucleotide polymorphism typing method, the DigiTag2 assay. Anal Biochem 2007; 364:78-85). Probes for detection are divided into a 3' probe (common probe) lying adjacent to and downstream of the SNP position, and a 5' probe (query probe) lying upstream of the SNP position and comprising the SNP at the 3' end. Two types of query probe are prepared which correspond to the respective alleles relevant to the SNP. Depending on the genotype of the SNP corresponding to the 3' end base of the query probe, only the query probe having a complementary base thereto can bind to the common probe lying adjacent to the 3' side of the SNP position. For detection, two query tags are attached at the 5' end of each of the two query probes in correspondence with the allele, and a different common tag for a different SNP is attached at the 3' end of the common probe. Detection is performed using a DNA chip on which oligo DNAs having base sequences complementary to the common tags attached to the common probes are immobilized. The binding product of a query probe and a common probe formed according to the genotype of a sample is captured by an oligo DNA having a base sequence complementary to the common tag on the DNA chip. The respective genotypes of the SNPs are determined by introducing two fluorescent molecules corresponding to the query tags representing the respective alleles.

Primers and TaqMan® probes for determining the rs17047200 genotype by a real-time PCR method were designed from base sequences around rs17047200 using Primer Express software v3.0.1 (Applied Biosystems, Foster City, Calif.) (FIG. 4). Depending on the genotype of the SNP, a probe having a base complementary thereto is bound, followed by cleavage along with the PCR extension reaction, whereby the signals from the two different fluorescent dyes labeled to the respective alleles (VIC®, FAM™) are emitted and detected to determine the genotype of the SNP.

<Results>

Figure 5:
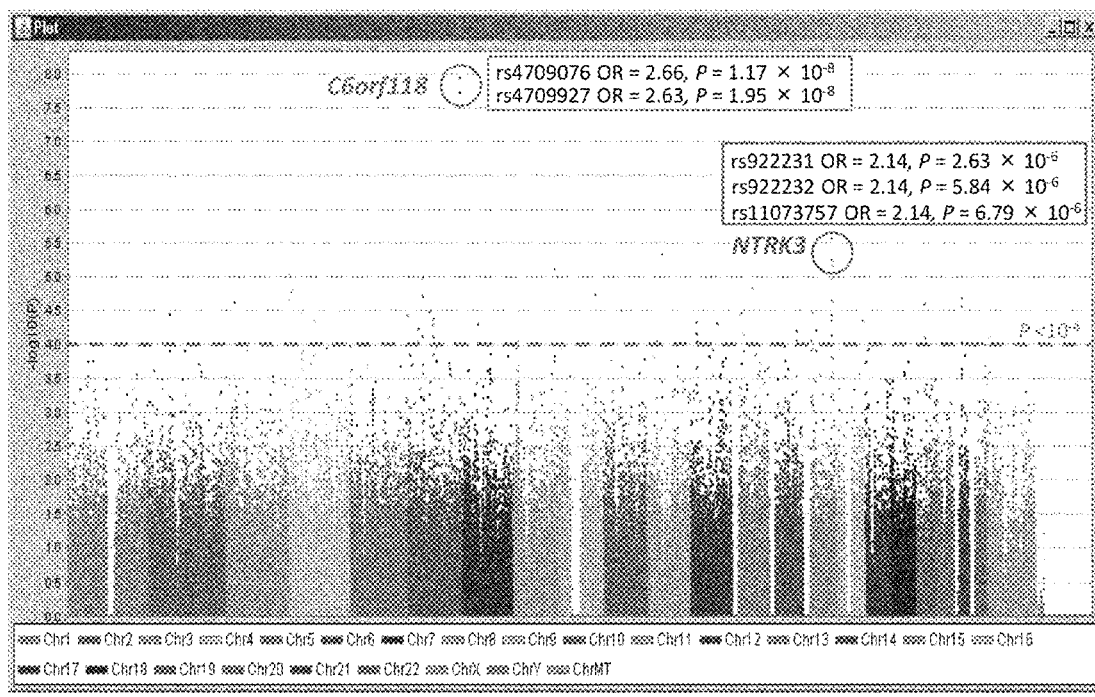
FIG. 5: Genome-wide association study (GWAS) results of 456 Japanese patients (Case, n=123; Control, n=333) (shown in a Manhattan plot). Each point indicates the P value by two-group comparison (chi-square test) for the allele frequency of a given SNP. 70 SNPs satisfied $P<10^4$, and higher-scoring SNPs among these formed two clusters (C6orf118 and NTRK3). HCC, hepatocellular carcinoma; SNP, single nucleotide polymorphism; OR, odds ratio; Chr, chromosome.
Figure 6:
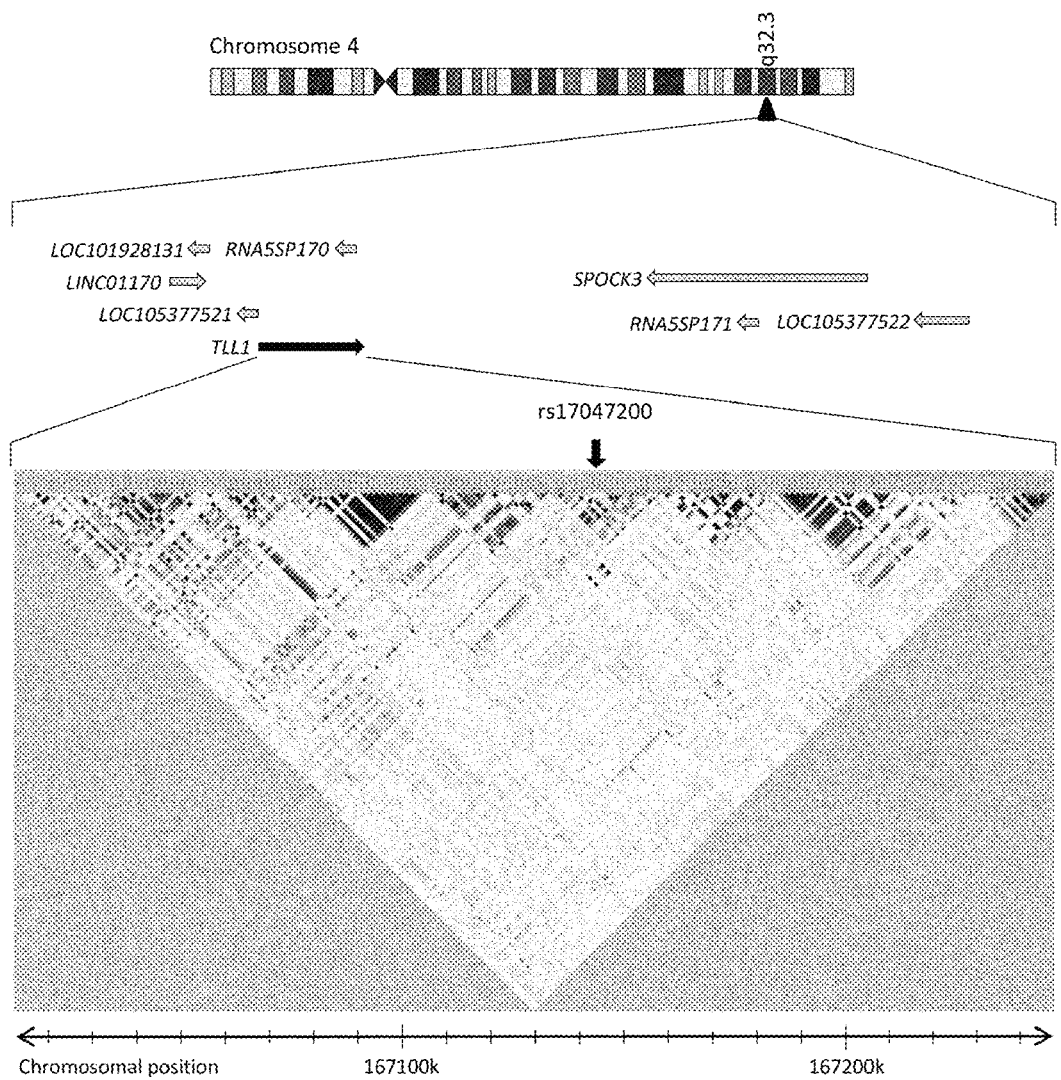
FIG. 6: Pairwise linkage disequilibrium ($r^2$) with tag SNPs located around the TLL1 locus on chromosome 4. The diagram was generated using the Japanese HapMap data.
Figure 8:
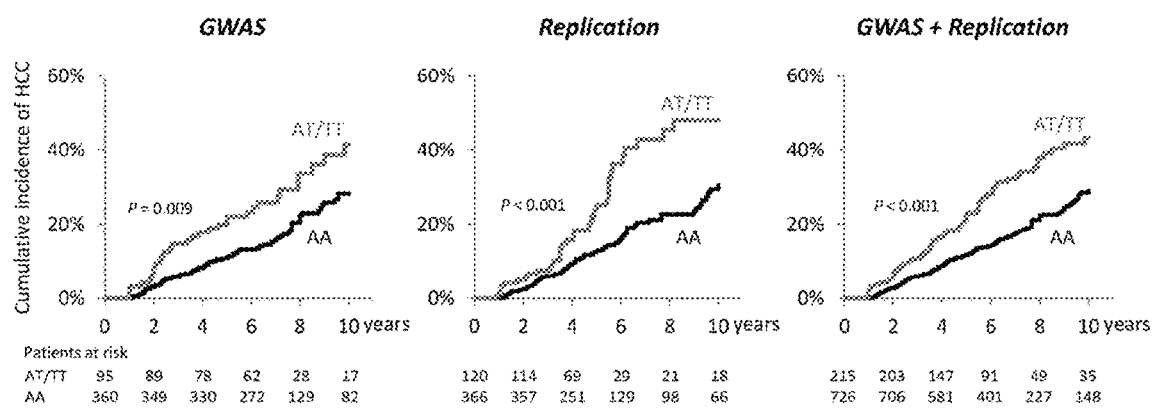
FIG. 8(A), FIG. 8(B), and FIG. 8(C): Cumulative incidence of hepatocellular carcinoma after the eradication of HCV according to rs17047200 genotype (using the Kaplan-Meier method). Both in the GWAS and in the replication study, results with a significantly higher incidence of carcinogenesis were obtained in the group AT/TT, relative to the group AA. P values were calculated by log rank testing. GWAS, genome-wide association study.

1. Identification of SNPs associated with the development of hepatocellular carcinoma after HCV eradication We conducted a GWAS to compare allele frequencies of 443,299 SNPs in G-Case (n=123) vs. G-CTRL (>5 y) (n=333), with the result that 70 SNPs were found to satisfy P<$10^{-4}$ (FIG. 5). Among these, the two top SNPs located downstream of C6orf118 on chromosome 6 met the genome-wide level of significance [rs4709076, odds ratio (OR)=2.66, P=1.17×$10^{-8}$; and rs4709927, OR=2.63, P=1.95×$10^{-8}$]. Furthermore, rs922231, rs922232, and rs11073757, which are located within NTRK3 on chromosome 15, also showed strong associations. Accordingly, firstly with respect to SNPs in these regions, a replication study was performed with 486 patients independent of those of the GWAS, but their replication was not observed. Then, a replication study was performed on 70 SNPs that satisfied P<$10^{-4}$ in the GWAS and 9 SNPs that previous reports had shown to be associated with HCV-related liver cirrhosis or hepatocellular carcinogenesis. In consequence, a replication of significance was observed with respect to rs17047200, which is located in the intron region of the TLL1 gene on chromosome 4 (FIG. 6). For this SNP, combining of the GWAS and replication study results revealed that it satisfied the genome-wide level of significance (OR=2.37, P=2.66×$10^{-8}$) (FIG. 7). When the cumulative incidence of carcinogenesis was examined by rs17047200 genotype, by means of the Kaplan-Meier method, both the GWAS and the replication study provided results showing that group AT/TT had a significantly higher incidence of carcinogenesis, relative to group AA (FIG. 8(A), FIG. 8(B), and FIG. 8(C)).

2. Risk Factors for the Development of Hepatocellular Carcinoma after HCV Eradication Next, a multivariate analysis of the risk of developing hepatocellular carcinoma after HCV eradication was performed using clinical data of all cases (n=942). It was revealed that in addition to male sex, older age, lower platelet count, advanced hepatic fibrosis, complicating diabetes, lower albumin level, and higher α-fetoprotein level, which are the previously reported risk factors, rs17047200 AT/TT was an independent risk factor [hazard ratio (HR)=1.78, P=0.008] (FIG. 9). Advanced hepatic fibrosis has been reported to be a major risk factor for carcinogenesis after HCV eradication. Thus, we examined the association between the carcinogenesis after HCV eradication and the rs17047200 genotype, according to the progression of hepatic fibrosis. In patients with mild hepatic fibrosis, the results from the multivariate analysis showed that older age (HR=2.90, P=0.001) and rs17047200 AT/TT (HR=4.26, P=0.005) were independent risk factors (FIG. 10). These risk factors were combined so as to divide the carcinogenic risk after HCV eradication into three groups (FIG. 11A). In patients with advanced hepatic fibrosis, the results from the multivariate analysis showed that higher α-fetoprotein level (after the end of treatment) (HR=1.90, P<0.001), lower albumin level (HR=0.43, P=0.004), and rs17047200 AT/TT (HR=1.86, P=0.017) were independent risk factors (FIG. 12). These risk factors were combined so as to divide the carcinogenic risk after HCV eradication into two groups (by the total number of risk factors) (FIG. 11B).

3. Analysis of TLL1 expression

Figure 14:
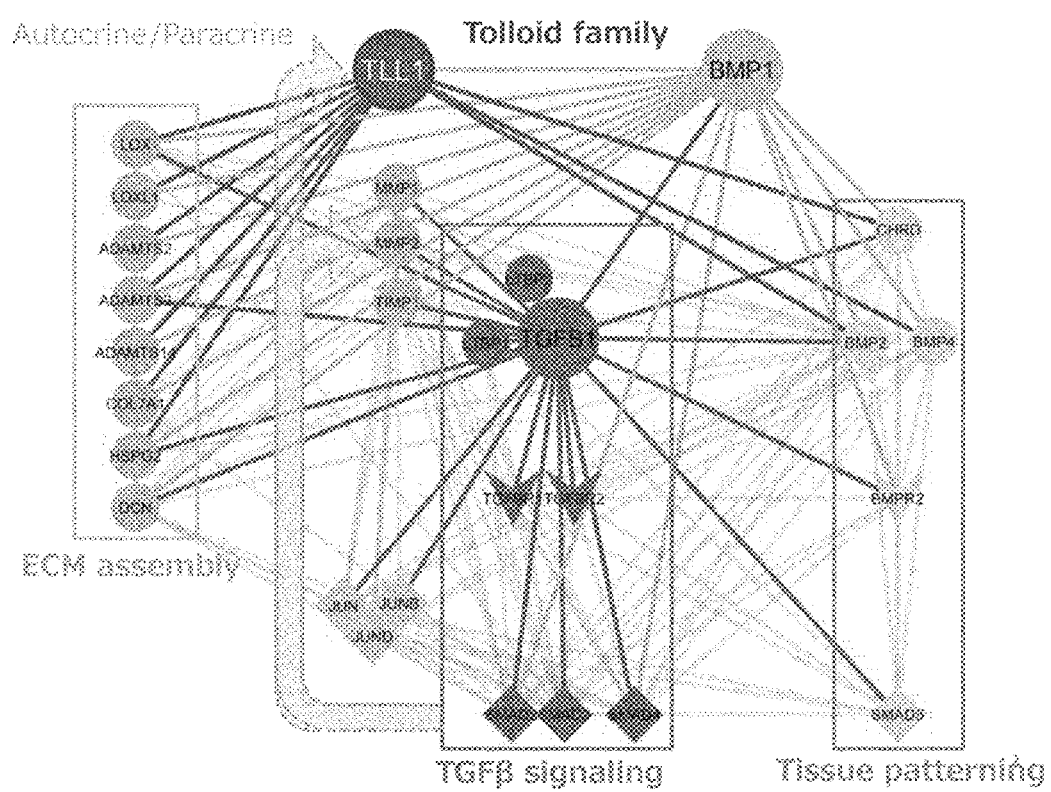
FIG. 14: Scheme for pathways involving TLL1 and BMP1. TLL1/BMP1 is deeply related to extracellular matrix (ECM) assembly and TGF-β signaling which play important roles in fibrosis. Receptors are represented by arrowheads, transcription factors by diamonds, and others by circles.
Figure 15:
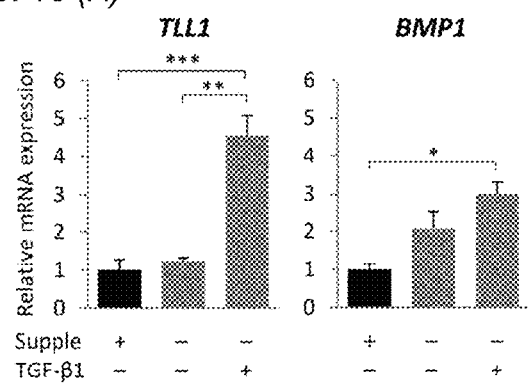
FIG. 15(A), FIG. 15(B), and FIG. 15(C): Gene expression levels of TLL1/BMP1 (Tll1/Bmp 1) in human hepatic stellate cells and hepatic fibrosis model rats. A: Human hepatic stellate cell line (HHSteC) cells were treated with human recombinant TGF-β1 (5 ng/ml). Three independent experiments were carried out. Data are presented as mean±standard error of the mean (n=3). The TLL1 mRNA level was elevated with the activation of hepatic stellate cells by TGF-β1. B: Hepatic fibrosis stages (METAVIR fibrosis stages) as determined by Heidenhain's azan staining. In contrast to liver tissues (at stage F0) of rats fed choline-supplemented methionine-reduced (CSAA) diets, remarkable hepatic steatosis and fibrosis were observed in liver tissues (at stages F2/F3-4) of rats fed choline-deficient methionine-reduced (CDAA) diets. C: The Tll1 mRNA level in liver tissues of hepatic fibrosis model rats was elevated with the progression of hepatic fibrosis. Data are presented as mean±standard error of the mean (n=5). * $P<0.05$,  $P<0.01$, * $P<0.001$.
Figure 15:
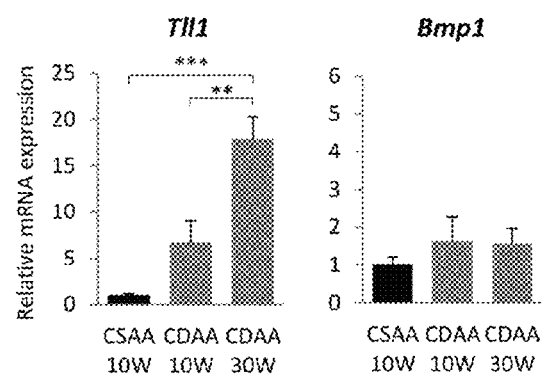
Figure 15:
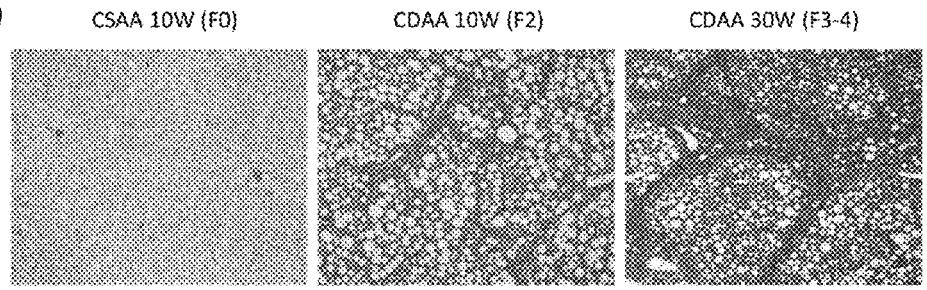
Figure 16:
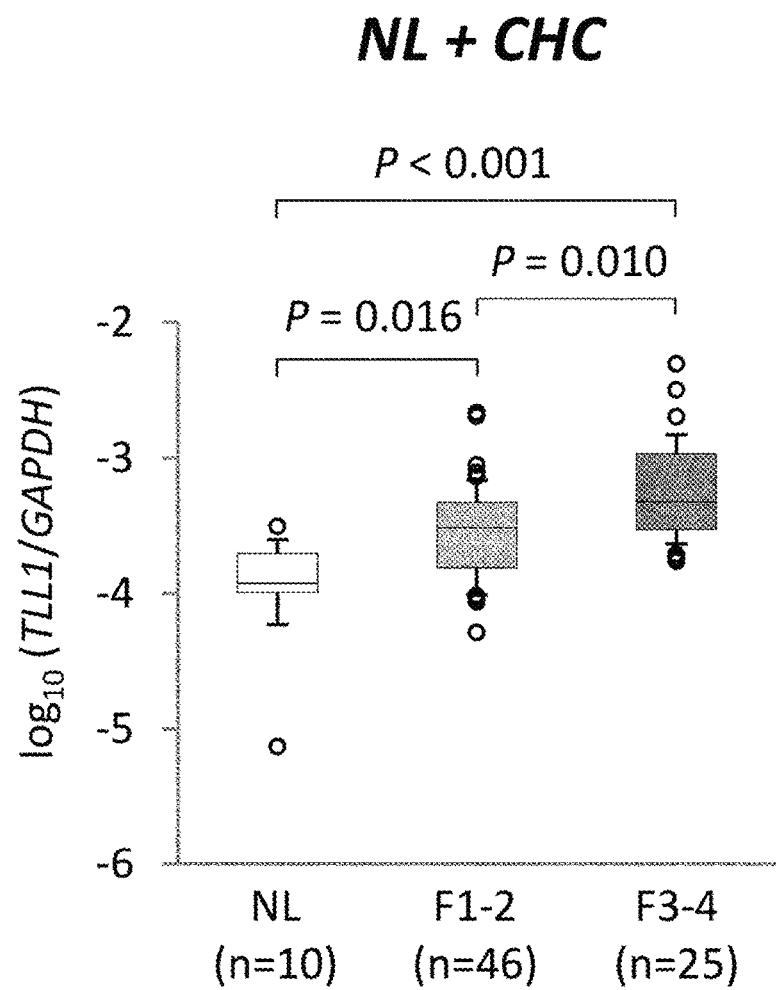
FIG. 16: TLL1 expression analyses in normal liver tissues and in liver tissues of patients with hepatitis C. The TLL1 mRNA level in NL (normal liver: non-tumor liver tissues surrounding metastatic liver tumor tissues) and in liver tissues of patients with hepatitis C was increased with the progression of hepatic fibrosis.
Figure 18:
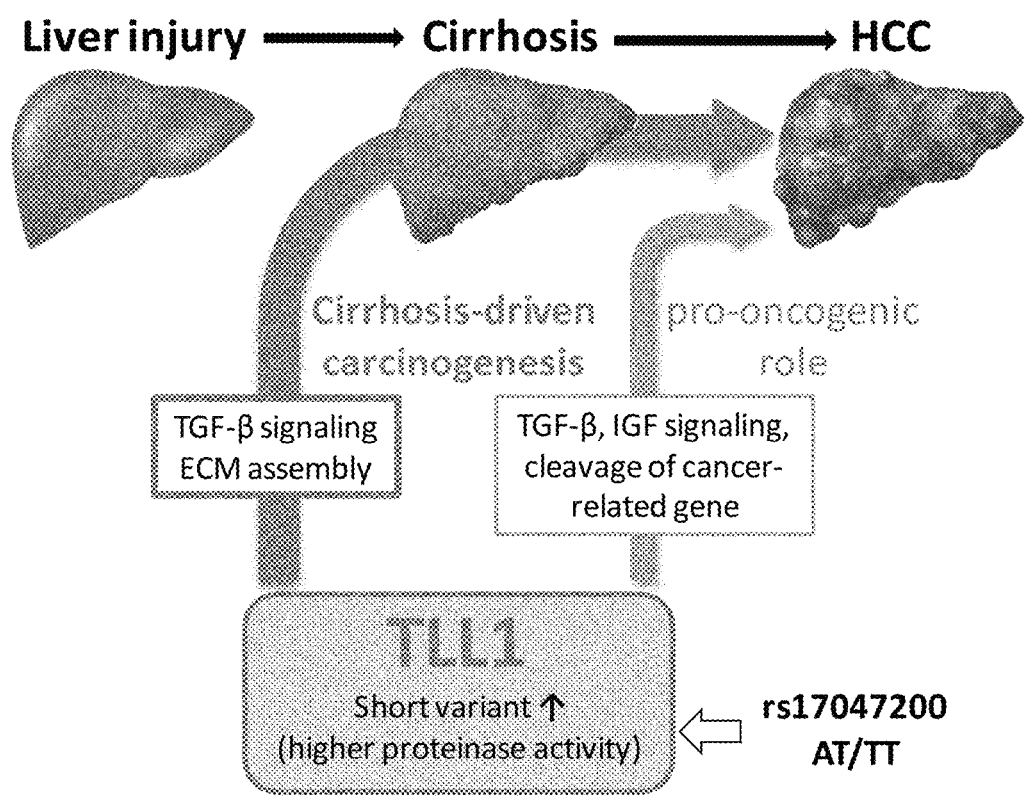
FIG. 18: Scheme for the roles of TLL1 in hepatocarcinogenesis. Patients with rs17047200 AT/TT were found to highly express the TLL1 short variants, suggesting that higher proteinase activity resulting from their high expression might promote the cirrhosis-driven carcinogenesis.

Mammalian Tolloid-like 1 (mTLL1) is a member of the bone morphogenetic protein 1/tolloid (BMP1/TLD)-like proteinase family, and in silico analysis of proteins interacting with TLL1 and BMP1 revealed that they are involved in extracellular matrix assembly and TGF-β signaling (FIG. 14). Since these are known to be deeply involved in fibrogenesis in various organs, an analysis of TLL1 expression was performed using a human hepatic stellate cell line, an animal model of hepatic fibrosis, and human liver tissue samples. When TGF-β1 was added to the culture supernatant of human hepatic stellate cell line (HHSteC) cells, the TLL1 mRNA level was increased similarly to ACTA2, which is an indicator of stellate cell activation (FIG. 15A). Next, an analysis was carried out using model rats in which hepatic fibrosis/carcinogenesis was brought about from nonalcoholic steatohepatitis (NASH) by administration of choline-deficient methionine-defined (CDAA [choline-deficient L-amino acid-defined]) diets. (FIG. 15B) It was found that the Tll1 mRNA level was increased with the progression of hepatic fibrosis (FIG. 15C). Similar tendencies were observed in studies using human normal liver tissues (noncancerous liver tissues surrounding metastatic liver cancer tissues) and liver tissues of patients with chronic hepatitis C (FIG. 16). That is, TLL1 was strongly induced with the activation of hepatic stellate cells or the progression of liver fibrosis, suggesting that the TLL1 gene might contribute to hepatocarcinogenesis mainly through advanced hepatic fibrosis since it is previously known that liver cancer (hepatocellular carcinoma) is likely to develop from an advanced state of hepatic fibrosis (liver cirrhosis) (FIG. 18).

Figure 17:
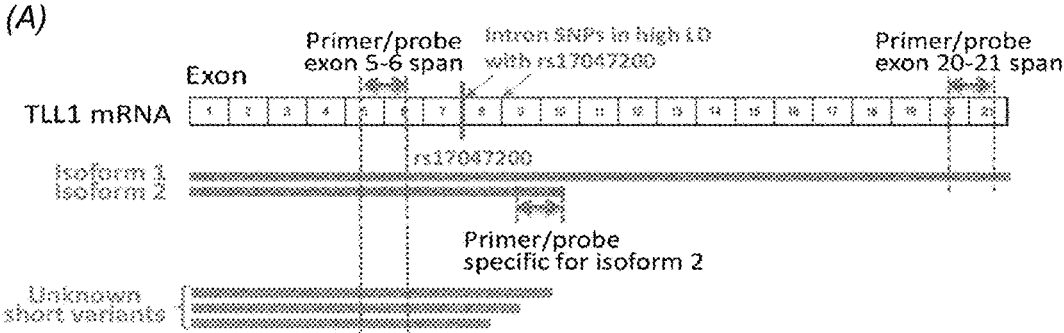
FIG. 17(A), FIG. 17(B), and FIG. 17(C): Expression study of TLL1 mRNA splice variants. A: Schematic diagram of TLL1 splice variants, and design of primers and probes for quantitative real-time PCR. Isoform 1 is a full-length TLL1, and isoform 2 is a previously reported short splice variant (GeneBank Accession: BC016922.2). B: Relative expression levels of short variants were compared by rs17047200 genotype, by calculating the proportion of the mRNA expression values obtained by real-time PCR, of exons 5 to 6 and exons 20 to 21 in non-tumor (NT) and tumor (T) tissues of patients who had developed liver cancer (hepatocellular carcinoma) after the eradication of HCV.C) Primers/probes specific for the previously reported isoform 2 were designed to compare its expression levels by rs17047200 genotype. In both analyses, the expression of the short variants was found to tend to be higher patients with rs17047200 AT/TT.
Figure 17:
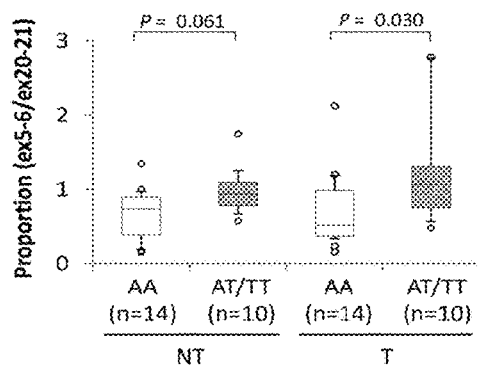
Figure 17:
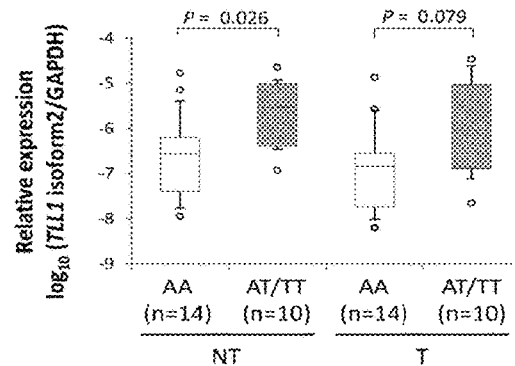

Next, the level of TLL1 mRNA (from the region of exons 5-6) in liver tissues of patients with hepatitis C was examined by rs17047200 genotype, but no differences were observed with respect to the rs17047200 genotypes. Since rs17047200 is located in the intron region of the TLL1 gene, we supposed that a significant SNP(s) in linkage disequilibrium with rs17047200 might be present in the promoter or exon regions of the TLL1 gene and affect the function of the TLL1 gene (protein expression), and examined this possibility by using SNP imputation procedures. However, no significant SNPs were found in these regions, while only several significant intron SNPs were found around rs17047200. From these results, we supposed that these intron SNPs, including rs17047200, might affect the splicing of TLL1 mRNA, and examined the expression of its short variants. Relative expression levels of short variants were compared by rs17047200 genotype, by calculating the proportion of the expression values obtained by real-time PCR of exons 5 to 6 and exons 20 to 21 in the non-tumor and tumor tissues of patients who had developed liver cancer (hepatocellular carcinoma) after SVR had been achieved. In addition, primers/probes specific for the previously reported TLL1 isoform 2 were designed to compare its expression levels by rs17047200 genotype, using real-time PCR. In both studies, it was found that rs17047200 AT/TT tended to result in a high level of expression of short variants (FIG. 17(A), FIG. 17(B), and FIG. 17(C)). Previous reports has shown that TLL1 short variants have higher proteinase activity than the full length TLL1 (Non-Patent Literature 22), and patients with rs17047200 AT/TT were found to highly express TLL1 short variants, suggesting that higher proteinase activity resulting from their high expression might promote the cirrhosis-driven carcinogenesis (FIG. 18).

<Discussion>

Figure 11:
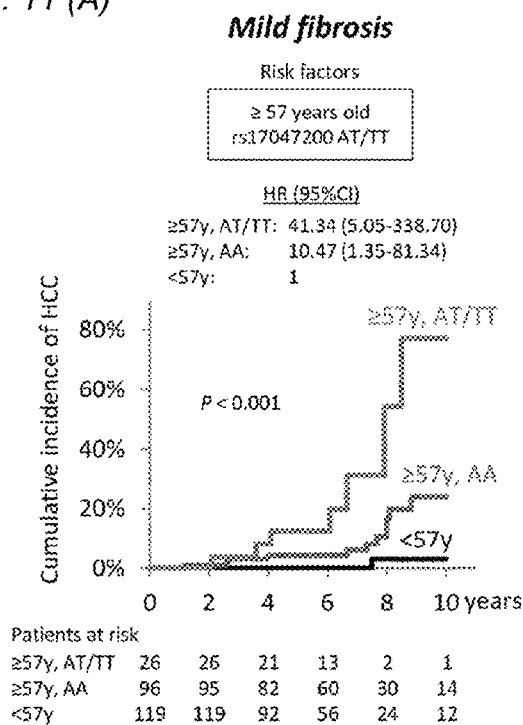
FIG. 11(A) and FIG. 11(B): Cumulative incidence of hepatocellular carcinoma according to degrees of hepatic fibrosis progression (using the Kaplan-Meier method). A) The risk factors for carcinogenesis in mild hepatic fibrosis were older age and rs17047200 AT/TT, which were combined so as to divide the carcinogenic risk into three groups. B) The risk factors for carcinogenesis in advanced hepatic fibrosis were higher a-fetoprotein level (at 24 weeks after the end of treatment), lower albumin level, and rs17047200 AT/TT, which were combined so as to divide the carcinogenic risk after HCV eradication into two groups (by the total number of risk factors combined). P values were calculated by log rank testing. Post, post-treatment (24 weeks after the end of treatment); AFP, α-fetoprotein; HCC, hepatocellular carcinoma.
Figure 11:
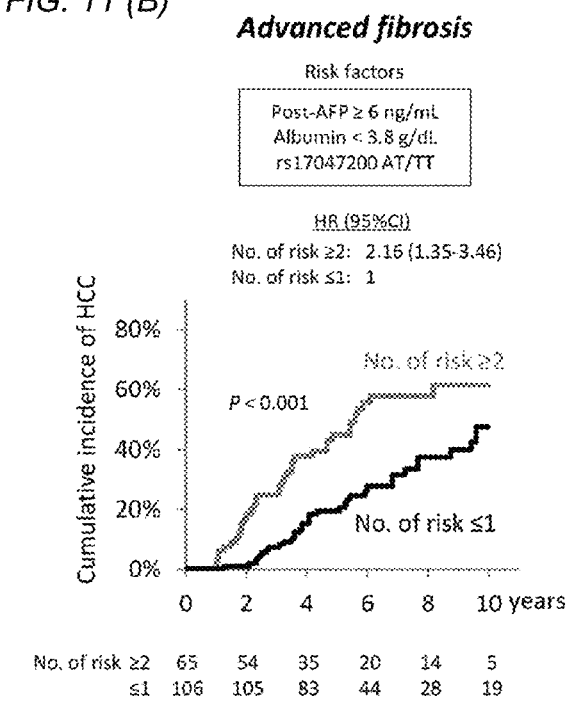
Figure 19:
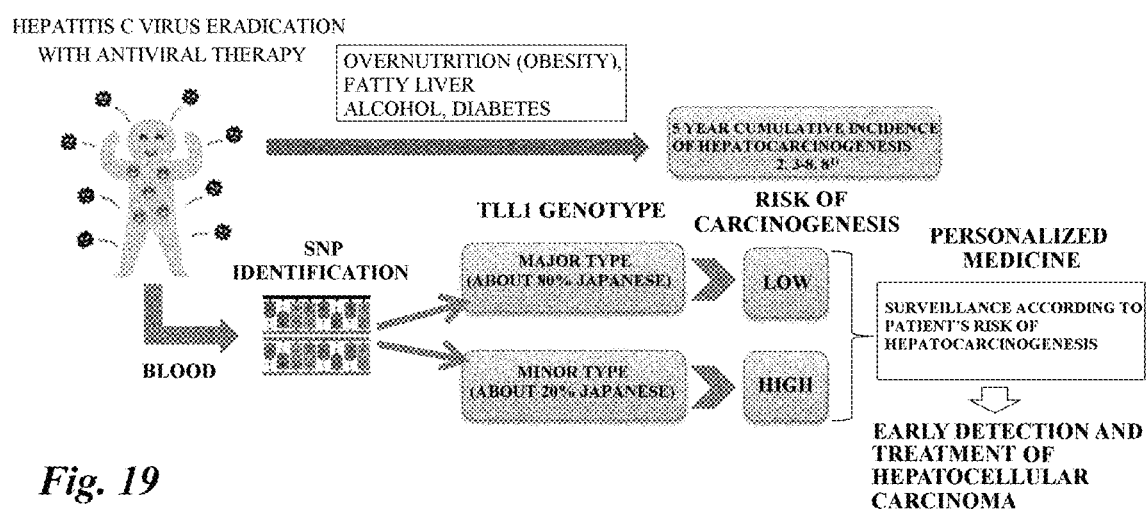
FIG. 19: Clinical application of the TLL1 gene polymorphism. The distribution of the TLL1 genotype is based on data from the International HapMap Project.

We conducted a comprehensive genome-wide analysis of SNPs involving the development of hepatocellular carcinoma after HCV eradication in Japanese patients who had achieved the eradication of HCV with interferon therapy, with the result that a SNP showing a strong association, which satisfied a genome-wide level of significance, was found. There has been no report so far on SNPs associated with the development of hepatocellular carcinoma after HCV eradication; this is the first report in the world. In these days when improvements in therapeutic treatments make it possible to achieve the eradication of HCV virus in most patients with HCV infection, a most important issue after the virus eradication is surveillance for carcinogenesis. Particularly in Japan, compared to the U.S. and European countries, patients with HCV infection are older and more often suffer from advanced hepatic fibrosis, and thus are presumed to have a higher incidence of hepatocellular carcinoma after HCV eradication. Therefore, there is a desire to establish a more accurate predictive method for carcinogenesis after HCV eradication. The genotype of rs17047200, a SNP which has been identified in this study, can be used as a predictive marker for hepatocellular carcinogenesis after HCV eradication, thereby to narrow down a group of high risk patients. Further, we constructed a model for more clearly predicting the carcinogenesis after HCV eradication, by combining the SNP with previously reported risk factors (FIG. 11). These successes make it possible to develop individualized medicine, such as carcinogenesis surveillance, according to risk (FIG. 19). Assuming that in the future, the determination of the rs17047200 genotype is practically applied clinically, we designed, from base sequences around rs17047200, primers and probes necessary for SNP typing by a real-time PCR method, with good results being obtained. From the above-mentioned background, there is an extremely large number of patients to be subjected to the determination of the rs17047200 genotype, and thus this clinical meaning would be of significance. In addition, it is expected that further research focusing on TLL1 will allow one to elucidate the mechanism of hepatocarcinogenesis after HCV eradication or due to other liver diseases (hepatitis B, NASH, etc.), and to develop novel therapeutic treatments. The distribution of genotypes and allele frequencies of the rs17047200 polymorphism is similar among various ethnic groups (except for African groups) (FIG. 13). This fact indicates that the rs17047200 polymorphism is highly versatile as a predictive marker for hepatocarcinogenesis after HCV eradication.

INDUSTRIAL APPLICABILITY

According to the present invention, it is possible to determine the risk of developing HCC after HCV eradication. The present invention makes it possible to narrow down patients who are likely to develop HCC in the future and to perform selective and intensive surveillance thereof. Therefore, early and timely therapeutic intervention will become available, whereby it can be expected, for example, to avoid the condition getting more serious and to enhance treatment effects. The present invention can be used in preventive medicine, and is also expected to contribute to medical economy by preventing unnecessary medical procedures.

The present invention is not limited to the description of the embodiments and working examples of the above-described invention in any way. The present invention includes various modifications that can be easily arrived at by a person skilled in the art without departing from the scope of the description of the claims. The contents of the articles, published patent publications, patent publications and the like explicitly specified in the present specification shall be cited by incorporating the entire contents thereof.

SEQUENCE LISTING FREE TEXT

SEQ ID NO: 2: Description of artificial sequence: forward primer

SEQ ID NO: 3: Description of artificial sequence: reverse primer

SEQ ID NO: 4: Description of artificial sequence: query probe for major allele

SEQ ID NO: 5: Description of artificial sequence: query probe for minor allele

SEQ ID NO: 6: Description of artificial sequence: common probe

SEQ ID NO: 7: Description of artificial Sequence: forward primer

SEQ ID NO: 8: Description of artificial sequence: reverse primer

SEQ ID NO: 9: Description of artificial sequence: probe for major allele

SEQ ID NO: 10: Description of artificial sequence: probe for minor allele

The invention claimed is:

1. A method for identifying a subject having a high risk of developing hepatocellular carcinoma after hepatitis C virus eradication comprising:
   (i) obtaining a biological sample from a subject that has previously undergone treatment sufficient to achieve a sustained virological response to hepatitis C virus, wherein the subject is an ethnically Mongoloid subject;
   (ii) deriving a genomic DNA sample from the biological sample;
   (iii) detecting the AT or TT genotype at SNP rs17047200 in the genomic DNA sample, wherein detecting is performed with a nucleic acid probe that is one of SEQ ID NO: 4, 5, 9, or 10;
   (iv) classifying the subject into Group 1 if the subject has stage 0-2 hepatic fibrosis or classifying the subject into Group 2 if the subject has stage 3-4 hepatic fibrosis;
   (v) measuring the level of albumin and α-fetoprotein if the subject is classified into Group 2 and detecting a high albumin level and a low α-fetoprotein level; and
   (vi) identifying the subject as having a high risk of developing hepatocellular carcinoma after hepatitis C virus eradication when (a) the subject has the AT or TT genotype at SNP rs17047200, belongs to Group 1, and has an older age or (b) the subject has the AT or TT genotype at SNP rs17047200, belongs to Group 2, has high albumin levels, and has low α-fetoprotein levels.

2. The method according to claim 1, wherein the risk associated with SNP rs17047200 is in the following order: risk in the case of AA<risk in the case of type AT<risk in the case of type TT.

3. The method according to claim 1, further comprising considering one or more risk factors for a subject belonging to Group 1 selected from the group consisting of male sex, lower platelet count, higher ALT level, higher γ-GTP level, and complicating diabetes.

4. The method according to claim 1, further comprising considering one or more risk factors for a subject belonging to Group 2 selected from the group consisting of older age, male sex, lower platelet count, higher ALT level, higher γ-GTP level, and complicating diabetes.

* * * * *